US 11,406,280 B2

United States Patent
Schleich et al.

(10) Patent No.: US 11,406,280 B2
(45) Date of Patent: Aug. 9, 2022

(54) METHOD FOR THE DIAGNOSIS OF AIRWAY DISEASE INFLAMMATORY SUBTYPE

(71) Applicants: UNIVERSITE DE LIEGE, Angleur (BE); CENTRE HOSPITALIER UNIVERSITAIRE DE LIEGE, Liege (BE); UNIVERSITEIT MAASTRICHT, Maastricht (NL)

(72) Inventors: Florence Schleich, Liege (BE); Renaud Louis, Liege (BE); Kyrylo Bessonov, Liege (BE); Kristel Van Steen, Liege (BE); Frederik-Jan Van Schooten, Maastricht (NL); Jan Dallinga, Maastricht (NL)

(73) Assignees: UNIVERSITE DE LIEGE, Angleur (BE); CENTRE HOSPITALIER UNIVERSITAIRE DE LIEGE, Liege (BE)

( * ) Notice: Subject to any disclaimer, the term of this patent is extended or adjusted under 35 U.S.C. 154(b) by 1178 days.

(21) Appl. No.: 15/761,520

(22) PCT Filed: Aug. 30, 2016

(86) PCT No.: PCT/EP2016/070346
§ 371 (c)(1),
(2) Date: Mar. 20, 2018

(87) PCT Pub. No.: WO2017/050527
PCT Pub. Date: Mar. 30, 2017

(65) Prior Publication Data
US 2020/0345266 A1    Nov. 5, 2020

(30) Foreign Application Priority Data
Sep. 21, 2015  (EP) .................................. 15185986

(51) Int. Cl.
*A61B 5/08* (2006.01)
*A61B 5/097* (2006.01)
(Continued)

(52) U.S. Cl.
CPC .............. *A61B 5/082* (2013.01); *A61B 5/097* (2013.01); *G01N 30/7206* (2013.01); *G01N 33/497* (2013.01)

(58) Field of Classification Search
CPC .... A61B 5/082; A61B 5/097; G01N 30/7206; G01N 33/497; G01N 2033/4975
See application file for complete search history.

(56) References Cited

U.S. PATENT DOCUMENTS

2010/0137733 A1   6/2010  Wang et al.
2016/0007913 A1*  1/2016  Darket ................. A61B 5/0022
                                              600/538
2016/0331270 A1* 11/2016  Yumoto ............... A61B 5/7278

FOREIGN PATENT DOCUMENTS

EP        2 273 265 A1    1/2011
WO    WO-2010031788 A1 *  3/2010    ......... G01N 33/5091
(Continued)

OTHER PUBLICATIONS

Kusano, Maiko. "Comparison of medical and forensic profiling potential of volatile biomarkers from different biological specimens from individuals and across populations." (2010) (Year: 2010).*
(Continued)

*Primary Examiner* — Christian Jang
(74) *Attorney, Agent, or Firm* — Jacobson Holman PLLC

(57) ABSTRACT

In vitro methods for diagnosing, prognosing and/or monitoring and treating neutrophilic or eosinophilic airway inflammation in a subject, including determining the amount of one or more volatile organic compounds (VOCs) in
(Continued)

exhaled breath from said subject. The invention also provides devices for use in said methods.

2 Claims, 12 Drawing Sheets

(51) Int. Cl.
*G01N 30/72* (2006.01)
*G01N 33/497* (2006.01)

(56) References Cited

FOREIGN PATENT DOCUMENTS

| WO | WO-2010149749 A1 | * | 12/2010 | ........... G01N 33/497 |
| WO | 2012/059763 A1 | | 5/2012 | |
| WO | WO-2012059763 A1 | * | 5/2012 | ......... G01N 33/6893 |
| WO | 2014/180974 A1 | | 11/2014 | |

OTHER PUBLICATIONS

Buist, A. S. "Similarities and differences between asthma and chronic obstructive pulmonary disease: treatment and early outcomes." European respiratory journal 21.39 suppl (2003): 30s-35s (Year: 2003).*

Corradi, Massimo, et al. "Aldehydes and glutathione in exhaled breath condensate of children with asthma exacerbation." American journal of respiratory and critical care medicine 167.3 (2003): 395-399 (Year: 2003).*

Moldoveanu, Serban C., Coleman WM III, and Niraj P. Kulshreshtha. "Evaluation of the Effect of Phytol on the Formation of PAHs in Cigarette Smoke." Beiträge zur Tabakforschung International/Contributions to Tobacco Research 24.1 (2010): 10-23 (Year: 2010).*

European Office Action dated Aug. 6, 2020.

Schleich et al. Volatile Organic Compounds Discriminate Between Eosinophilic and Neutrophilic Inflammation In Vitro. J.Breath Res. 10 (2016) 016006. XP55719244A.

European Office Action dated May 3, 2019.

Schleich et al. Distribution of sputum cellular phenotype in a large asthma cohort; predicting factors for eosinophilic vs neutrophilic inflammation. BMC Pulmonary Medicine, Biomed Central, vol. 13, No. 1, Feb. 26, 2013, p. 11, XP021150850, ISSN: 1471-2466.

International Search Report, dated Dec. 8, 2016 (4 pages).

* cited by examiner

METHOD FOR THE DIAGNOSIS OF AIRWAY DISEASE INFLAMMATORY SUBTYPE

FIELD OF THE INVENTION

The present invention relates to in vitro methods of diagnosing, prognosing and/or monitoring neutrophilic or eosinophilic airway inflammation in a subject, comprising determining the amount of one or more volatile organic compounds (VOCs). The invention further relates to methods of discriminating between different subtypes of airway inflammation comprising determining the amount of one or more VOCs.

BACKGROUND OF THE INVENTION

Inflammatory airway diseases are typically of a chronic nature. They increase morbidity and may, ultimately, cause death. They include a range of diseases including, but not limited to, asthma, bronchitis, chronic obstructive pulmonary disease (COPD), cystic fibrosis, emphysema or acute respiratory distress syndrome. It has become apparent that asthma is a complex disease of the airways with many different underlying mechanisms. It is now considered as a syndrome containing several subtypes with similarities and differences caused by variable underlying etiologies. There are four distinct inflammatory subtypes of asthma: eosinophilic, neutrophilic, mixed granulocytic and paucigranulocytic subtypes. Induced sputum (i.e. mucus that is coughed up from the lower airways) followed by differential cell count is currently one of the only available minimally invasive assessments of inflammatory subtypes in asthma. Hence, in the art, patients are classified in four inflammatory subtypes according to the result of their sputum cell count, i.e. eosinophilic subtype ($\geq 3\%$ eosinophils in the sputum), neutrophilic subtype ($\geq 76\%$ neutrophils), mixed granulocytic subtype ($\geq 3\%$ eosinophils and $\geq 76\%$ neutrophils) and paucigranulocytic subtype ($<3\%$ eosinophils and $<76\%$ neutrophils) (Louis et al.: Induced Sputum—Towards Normal Values. Non Invasive Assessment of airways inflammation in asthma and COPD. 14th, tetrapoleos street, Athens, 115 27, Greece: Paschalidis Medical Publications; 2011: 113-123. ISBN 978-960-489-104-7 Chapter 7).

In the past, treatment options for asthma were limited and the characterization of subtypes was not required. Since new therapies have appeared, there is a need to characterize asthma subtypes to better orient treatments and avoid putative side effects of misused therapies. As an example, anti-IL5 treatment does not significantly improve an unselected population of severe asthmatics while it improves asthma control and reduced exacerbation in selected patients exhibiting eosinophilic subtype (Castro et al, Am. J. Respir. Crit. Care Med. 184:1125-1132). Other important studies have confirmed that eosinophilic airway inflammation most reliably predicts the response to anti-inflammatory treatment such as inhaled corticosteroids (ICS) (Pavord at al, Lancet 353:2213-2214) and anti-IL5 (Haldar et al, N. Engl. J. Med. 360:973-984). Numerous studies showed that regular treatments with ICS sharply and quickly reduce the percentage of eosinophils contained in the sputum from asthmatics and repress the release of Th2 cytokines from lymphocytes and eotaxin from epithelial cells. Hence ICS are particularly effective in combating Th2-driven inflammation featuring mast cell and eosinophilic airway infiltration. However their effect on innate immunity-driven neutrophilic inflammation is rather poor. Moreover ICS have been shown to be powerful inducers of neutrophil survival due to an inhibitory effect on human neutrophil apoptosis and are thereby not recommended to treat neutrophilic asthma (Meagher et al, J. Immunol. 156:4422-4428). On the other hand there is no evidence that ICS may improve short-term asthma control in the absence of uncontrolled eosinophilic inflammation as encountered in paucigranulocytic asthma (Pavord at al, Lancet 353:2213-2214). It has also been shown that severe neutrophilic asthma could be best targeted by using macrolides such as clarithromycin (Simpson et al, Am. J. Respir. Crit Care Med. 177:148-155). Anti-inflammatory properties of macrolides include a decrease in IL-8 and a reduction in neutrophils recruitment and activation.

Hence characterizing the inflammatory subtype in patients with airway inflammatory disease is crucial to orient treatment and avoid side effects. However inflammatory subtype determination using sputum collection is complex, time-consuming, unpleasant for the patient and not widely applicable because it requires significant technical expertise in experienced centers. Furthermore sputum samples cannot be obtained in at least 10% of attempts.

Hence there is a need for new methods for airway inflammatory diseases subtype determination that are non-invasive, simpler, faster, more accurate and cost-effective. Volatile organic compounds (VOCs) present in the exhaled breath were shown to be able to discriminate between various lung pathologies. Several studies have already suggested the usefulness of VOCs detection in exhaled air as a diagnostic tool in brain, prostate and lung cancer as well as in tuberculosis, asthma and COPD.

Hence, analysis of exhaled breath for determination of inflammatory subtype in airway inflammation using endogenous volatile organic compounds could offer the possibility of noninvasive diagnosis and therapeutic monitoring. Fractional exhaled nitric oxide (FENO) measurement in exhaled air is for example an option for diagnosis and monitoring asthma. Moreover, FENO is able to identify a sputum eosinophil count $\geq 3\%$ with reasonable accuracy if different thresholds are used according to the dose of ICS, smoking status and atopy. On the other hand, WO2012/059763 discloses a method of diagnosing COPD and asthma, as well as particular sub-groups thereof, by analyzing exhaled breath samples for VOCs. 35 asthmatic patients were studied, with 18 patients able to provide induced sputum sample for inflammatory subtype determination. In particular, WO2012/059763 provides methods of diagnosing individuals with asthma that have elevated (>40%) neutrophil levels or elevated (>2%) eosinophil levels. On the other hand, WO2012/059763 does not provide VOCs markers able to discriminate between several asthma subtypes in the same test.

There is, therefore, an unmet need for improved methods using VOCs markers for the diagnosis, prognosis and monitoring of the subtype of airway inflammation based on large populations of patients, as well as on standard definitions of subtypes of airway inflammation described in the art. Moreover, there is an unmet need for methods using VOCs markers able to discriminate between several subtypes of airway inflammation in the same test, which would allow rapid adaptation of patient's treatment.

SUMMARY OF THE INVENTION

Airway inflammation, such as asthma, is a complex disease with many inflammatory subtypes, which do not respond to the same therapies in the same way, both in terms of efficacy and adverse reactions. For example, inhaled corticosteroids are efficient to treat eosinophilic asthma, but do not improve paucigranulocytic asthma, and have poor or even detrimental effects on neutrophilic asthma. On the other hand, neutrophilic asthma can be best targeted using macrolides such as clarithromycin. Determination of subtypes of airway inflammation in patients is therefore crucial for adapting the treatment to reach inflammation control with reduction of future risks.

Having conducted extensive experiments and tests, the inventors have found that specific exhaled volatile organic compounds (VOCs) can be used as markers for diagnosis, prognosis and/or monitoring subtypes of airway inflammation, such as neutrophilic or eosinophilic airway inflammation. The inventors have furthermore demonstrated that exhaled VOCs can be used for the discrimination between different subtypes of airway inflammation.

As shown in detail in the example section, the inventors collected VOCs from the exhaled breath of a large number of asthmatic patients (276 asthmatics, that were sampled with 3327 VOCs detected). Patient's asthma subtype was determined by counting inflammatory cells in patient's induced sputum. Then patients were classified as suffering from eosinophilic asthma (≥3% eosinophils in the sputum), neutrophilic asthma (≥76% neutrophils) and paucigranulocytic asthma (<3% eosinophils and <76% neutrophils, i.e. normal levels of eosinophils and neutrophils). Special attention has been paid to classify patients according to standard definitions of asthma subtypes (Louis et al.: Induced Sputum—Towards Normal Values. Non Invasive Assessment of airways inflammation in asthma and COPD. 14th, tetrapoleos street, Athens, 115 27, Greece: Paschalidis Medical Publications; 2011: 113-123. ISBN 978-960-489-104-7 Chapter 7). In contrast of the method disclosed in WO2012/059763, only patients with ≥76% neutrophils in the sputum are classified as neutrophilic asthmatics, and only patients with ≥3% eosinophils in the sputum are classified as eosinophilic asthmatics, thereby avoiding to confuse them with paucigranulocytic asthmatic, which can lead to misdiagnosing.

Using this classification method, 122 patients exhibited eosinophilic asthma, 90 had paucigranulocytic asthma and 50 neutrophilic asthma.

Gas chromatography and time-of-flight mass spectrometry was used to identify VOCs present in exhaled breath from these patients. Extended statistical analysis was performed to determine the best VOC or combination of VOCs to allow accurate diagnosis, prognosis, monitoring or discrimination of asthma subtype.

Provided herein is an in vitro method of diagnosing, prognosing and/or monitoring neutrophilic airway inflammation in a subject, comprising determining the amount of one or more volatile organic compounds (VOCs) selected from the group consisting of:
3-tetradecene ($C_{14}H_{28}$),
1-pentadecene ($C_{15}H_{30}$),
3,7-dimethylnonane ($C_{11}H_{24}$),
nonanal ($C_9H_{18}O$), and
1-propanol ($C_3H_8O$),
in a sample of exhaled breath from said subject.

In a preferred embodiment, 3-tetradecene ($C_{14}H_{28}$) and/or 1-pentadecene ($C_{15}H_{30}$) amounts are elevated in exhaled breath from patients suffering from neutrophilic airway inflammation compared to exhaled breath from patients suffering from paucigranulocytic inflammation.

In another preferred embodiment, 3,7-dimethylnonane ($C_{11}H_{24}$), nonanal ($C_9H_{18}O$) and/or 1-propanol ($C_3H_8O$) amounts are elevated in exhaled breath from patients suffering from neutrophilic airway inflammation compared to those suffering from eosinophilic airway inflammation.

Paucigranulocytic and eosinophilic airway inflammation are characterized by normal levels of neutrophils in the airways, comparable to that in healthy subjects (Louis et al.: Induced Sputum—Towards Normal Values. Non Invasive Assessment of airways inflammation in asthma and COPD. 14th, tetrapoleos street, Athens, 115 27, Greece: Paschalidis Medical Publications; 2011: 113-123. ISBN 978-960-489-104-7 Chapter 7). Hence one or more of 3-tetradecene ($C_{14}H_{28}$), 1-pentadecene ($C_{15}H_{30}$), 3,7-dimethylnonane ($C_{11}H_{24}$), nonanal ($C_9H_{18}O$), and 1-propanol ($C_3H_8O$) can advantageously be used as markers of neutrophilic airway inflammation.

The invention also provides for an in vitro method of discriminating neutrophilic airway inflammation from paucigranulocytic airway inflammation in a subject, comprising the steps of:
a) Determining the amount of one or more volatile organic compounds (VOCs) selected from the group consisting of:
3-tetradecene ($C_{14}H_{28}$), and
1-pentadecene ($C_{15}H_{30}$),
in a sample of exhaled breath from said subject; and
b) Comparing said amount of one or more VOCs with a reference value.

The inventors found that 3-tetradecene ($C_{14}H_{28}$) and 1-pentadecene ($C_{15}H_{30}$) can be advantageously used to discriminate neutrophilic airway inflammation from paucigranulocytic airway inflammation with a very good classification accuracy (AUC of 0.8459). Each 3-tetradecene ($C_{14}H_{28}$) or 1-pentadecene ($C_{15}H_{30}$) also gave alone very good classification accuracy as exemplified in the example section.

Further provided herein is an in vitro method of discriminating neutrophilic airway inflammation from eosinophilic airway inflammation in a subject, comprising the steps:
a) Determining the amount of one or more volatile organic compounds (VOCs) selected from the group consisting of:
3,7-dimethylnonane ($C_{11}H_{24}$),
nonanal ($C_9H_{18}O$), and
1-propanol ($C_3H_8O$),
in a sample of exhaled breath from said subject; and
b) Comparing said amount of one or more VOCs with a reference value.

The inventors found that 3,7-dimethylnonane ($C_{11}H_{24}$), nonanal ($C_9H_{18}O$) and 1-propanol ($C_3H_8O$) can be advantageously used to discriminate neutrophilic airway inflammation from eosinophilic airway inflammation with an excellent classification accuracy (AUC of 0.9193). Each 3,7-dimethylnonane ($C_{11}H_{24}$), nonanal ($C_9H_{18}O$) or 1-propanol ($C_3H_8O$) also gave alone very good classification accuracy as exemplified in the example section.

The invention also provides for an in vitro method of diagnosing, prognosing and/or monitoring eosinophilic airway inflammation in a subject, comprising determining the amount of one or more volatile organic compounds (VOCs) selected from the group consisting of:
2-hexanone ($C_6H_{12}O$), and
hexane ($C_6H_{14}$)
in a sample of exhaled breath from said subject.

In a preferred embodiment, 2-hexanone ($C_6H_{12}O$) and/or hexane ($C_6H_{14}$) amounts are reduced in exhaled breath from patients suffering from eosinophilic airway inflammation compared to exhaled breath from patients suffering from paucigranulocytic airway inflammation.

Paucigranulocytic inflammation is characterized by normal levels of neutrophils in the airways, comparable to that of healthy subjects (Louis et al). Hence one or more of 2-hexanone (C6H12O) and hexane (C6H14) can advantageously be used as markers for eosinophilic airway inflammation.

The invention also provides for an in vitro method of discriminating eosinophilic airway inflammation from paucigranulocytic airway inflammation in a subject, comprising the steps:
a) Determining the amount of one or more volatile organic compounds (VOCs) selected from the group consisting of:
2-hexanone (C6H12O), and
hexane (C6H14),
in a sample of exhaled breath from said subject; and
b) Comparing said amount of one or more VOCs with a reference value.

The inventors found that 2-hexanone (C6H12O) and hexane (C6H14) can advantageously be used to discriminate eosinophilic airway inflammation from paucigranulocytic airway inflammation with an excellent classification accuracy (AUC of 0.9945). Each 2-hexanone (C6H12O) or hexane (C6H14) also gave alone very good classification accuracy as exemplified in the example section.

Also provided herein is a device for use in the methods according to the invention.

Thus, the present invention advantageously enables an accurate, non-invasive and simple in vitro method of and device for diagnosing, prognosing and/or monitoring neutrophilic or eosinophilic inflammation. The present invention also enables, in the same method or with the same device, the discrimination between clinically relevant subtypes of airway inflammation, hence providing rapid guidance to the medical practitioner about the best-targeted therapy to apply.

The invention hence provides the following aspects.

Aspect 1) An in vitro method of diagnosing, prognosing and/or monitoring neutrophilic airway inflammation in a subject, comprising determining the amount of one or more volatile organic compounds (VOCs) selected from the group consisting of:
3-tetradecene (C14H28),
1-pentadecene (C15H30),
3,7-dimethylnonane (C11H24),
nonanal (C9H18O), and
1-propanol (C3H8O),
in a sample of exhaled breath from said subject.

Aspect 2) The in vitro method according to aspect 1, wherein neutrophilic airway inflammation is characterized by a sputum neutrophils count greater than or equal to 70%, preferably greater than or equal to 76%, of the total white cells present in the sputum.

Aspect 3) The in vitro method according to aspect 1 or 2, wherein the method further comprises the steps of:
a) Comparing said amount of one or more VOCs with a reference value, said reference value representing a known diagnosis, prognosis and/or monitoring status of neutrophilic airway inflammation;
b) Finding a deviation or no deviation of the amount of said one or more VOCs from said reference value; and
c) Attributing said finding of deviation or no deviation to a particular diagnosis, prognosis and/or monitoring status of neutrophilic airway inflammation in the subject.

Aspect 4) The in vitro method according to aspect 3, wherein:
the reference value is the amount of the same one or more VOCs in a sample of exhaled breath from a subject selected from the group comprising: a subject suffering from paucigranulocytic airway inflammation, a healthy subject, and a subject suffering from eosinophilic airway inflammation; and wherein
a deviation of the amount, preferably an elevated amount, of said one or more VOCs from said reference value is diagnostic or prognostic of neutrophilic airway inflammation in the subject.

Aspect 5) The in vitro method according to aspect 3, wherein:
the reference value is the amount of the same one or more VOCs in a sample of exhaled breath from a subject suffering from neutrophilic airway inflammation; and wherein
no deviation of the amount of said one or more VOCs from said reference value is diagnostic or prognostic of neutrophilic airway inflammation in the subject.

Aspect 6) An in vitro method of discriminating neutrophilic airway inflammation from paucigranulocytic airway inflammation in a subject, comprising the steps of:
a) Determining the amount of one or more volatile organic compounds (VOCs) selected from the group consisting of:
3-tetradecene (C14H28), and
1-pentadecene (C15H30),
in a sample of exhaled breath from said subject; and
b) Comparing said amount of one or more VOCs with a reference value.

Aspect 7) The in vitro method according to aspect 6, wherein:
the reference value is the amount of the same one or more VOCs in a sample of exhaled breath from a subject suffering from paucigranulocytic airway inflammation; and wherein
an elevated amount of said one or more VOCs from said reference value is diagnostic or prognostic of neutrophilic airway inflammation and/or of absence of paucigranulocytic airway inflammation in the subject.

Aspect 8) The in vitro method according to aspect 6, wherein:
the reference value is the amount of the same one or more VOCs in a sample of exhaled breath from a subject suffering from neutrophilic airway inflammation; and wherein
no deviation of the amount of said one or more VOCs from said reference value is diagnostic or prognostic of neutrophilic airway inflammation and/or of absence of paucigranulocytic airway inflammation in the subject.

Aspect 9) An in vitro method of discriminating neutrophilic airway inflammation from eosinophilic airway inflammation in a subject, comprising the steps:
a) Determining the amount of one or more volatile organic compounds (VOCs) selected from the group consisting of:
3,7-dimethylnonane (C11H24),
nonanal (C9H18O), and
1-propanol (C3H8O),
in a sample of exhaled breath from said subject; and
b) Comparing said amount of one or more VOCs with a reference value.

Aspect 10) The in vitro method according to aspect 9, wherein:
the reference value is the amount of the same one or more VOCs in a sample of exhaled breath from a subject suffering from eosinophilic airway inflammation; and wherein
an elevated amount of said one or more VOCs from said reference value is diagnostic or prognostic of neutrophilic airway inflammation and/or of absence of eosinophilic airway inflammation in the subject.

Aspect 11) The in vitro method according to aspect 9, wherein:
the reference value is the amount of the same one or more VOCs in a sample of exhaled breath from a subject suffering from neutrophilic airway inflammation; and wherein
no deviation of the amount of said one or more VOCs from said reference value is diagnostic or prognostic of neutrophilic airway inflammation and/or of absence of eosinophilic airway inflammation in the subject.

Aspect 12) An in vitro method of diagnosing, prognosing and/or monitoring eosinophilic airway inflammation in a subject, comprising determining the amount of one or more volatile organic compounds (VOCs) selected from the group consisting of:
2-hexanone (C6H12O), and
hexane (C6H14),
in a sample of exhaled breath from said subject.

Aspect 13) The in vitro method according to aspect 12, wherein eosinophilic airway inflammation is characterized by a sputum eosinophils count greater than or equal to 3% of the total white cells present in the sputum.

Aspect 14) The in vitro method according to aspect 12 or 13, wherein the method further comprises the steps of:
a) Comparing said amount of one or more VOCs with a reference value, said reference value representing a known diagnosis, prognosis and/or monitoring status of eosinophilic airway inflammation; and
b) Finding a deviation or no deviation of the amount of said one or more VOCs from said reference value;
c) Attributing said finding of deviation or no deviation to a particular diagnosis, prognosis and/or monitoring status of eosinophilic airway inflammation in the subject.

Aspect 15) The in vitro method according to aspect 14, wherein:
the reference value is the amount of the same one or more VOCs in a sample of exhaled breath from a subject selected from the group comprising: a subject suffering from paucigranulocytic airway inflammation and a healthy subject; and wherein
a deviation of the amount, preferably a reduced amount, of said one or more VOCs from said reference value is diagnostic or prognostic of eosinophilic airway inflammation in the subject.

Aspect 16) The in vitro method according to aspect 14, wherein:
the reference value is the amount of the same one or more VOCs in a sample of exhaled breath from a subject suffering from eosinophilic airway inflammation; and wherein
no deviation of the amount of said one or more VOCs from said reference value is diagnostic or prognostic of eosinophilic airway inflammation in the subject.

Aspect 17) An in vitro method of discriminating eosinophilic airway inflammation from paucigranulocytic airway inflammation in a subject, comprising the steps:
a) Determining the amount of one or more volatile organic compounds (VOCs) selected from the group consisting of:
2-hexanone (C6H12O), and
hexane (C6H14),
in a sample of exhaled breath from said subject; and
b) Comparing said amount of one or more VOCs with a reference value.

Aspect 18) The in vitro method according to aspect 17, wherein:
the reference value is the amount of the same one or more VOCs in a sample of exhaled breath from a subject suffering from paucigranulocytic airway inflammation; and wherein
a reduced amount of said one or more VOCs from said reference value is diagnostic or prognostic of eosinophilic airway inflammation and/or of absence of paucigranulocytic airway inflammation in the subject.

Aspect 19) The in vitro method according to aspect 17, wherein:
the reference value is the amount of the same one or more VOCs in a sample of exhaled breath from a subject suffering from eosinophilic airway inflammation; and wherein
no deviation of the amount of said one or more VOCs from said reference value is diagnostic or prognostic of eosinophilic airway inflammation and/or of absence of paucigranulocytic airway inflammation in the subject.

Aspect 20) The in vitro method according to any one of aspects 1 to 19, wherein said amount of VOCs is determined using gas chromatography and/or mass spectrometry.

Aspect 21) The in vitro method according to any one of aspects 1 to 20, wherein airway inflammation is selected from the group comprising: asthma, chronic obstructive pulmonary disease, cystic fibrosis, emphysema, bronchitis, acute respiratory distress syndrome, bronchial constriction, coughing, phlegm, bronchial adenoma, pulmonary tuberculosis, pulmonary emphysema and lung abscess or combinations thereof. Preferred airway inflammation is asthma.

Aspect 22) A method of treatment of neutrophilic airway inflammation in a subject, comprising treating the subject, diagnosed as being in need of neutrophilic airway inflammation treatment according to the method of any one of aspects 1 to 11, with a treatment selected from the group consisting of: macrolides, anti-leukotriene agents, bronchodilators, corticosteroids and anti-interleukin 5 agents or combinations thereof. Preferably treatment is selected from the group consisting of: macrolides, anti-leukotriene agents and bronchodilators or combinations thereof.

Aspect 23) A method of treatment of neutrophilic airway inflammation in a subject, comprising the steps of:
a) Determining whether the subject is in need of receiving neutrophilic airway inflammation treatment comprising performing the method according to any one of aspects 1 to 11; and
b) Treating the subject diagnosed in step a) as being in need of neutrophilic airway inflammation treatment with a treatment selected from the group consisting of: macrolides, anti-leukotriene agents, bronchodilators, corticosteroids and anti-interleukin 5 agents or combinations thereof. Preferably treatment is selected from the group consisting of: macrolides, anti-leukotriene agents and bronchodilators or combinations thereof.

Aspect 24) A method of treatment of eosinophilic airway inflammation in a subject, comprising treating the subject, diagnosed as being in need of eosinophilic airway inflammation treatment according to the method of any one of aspects 12 to 19, with a treatment selected from the group consisting of: macrolides, anti-leukotriene agents, bronchodilators, corticosteroids and anti-interleukin 5 agents or combinations thereof. Preferably treatment is selected from the group consisting of: bronchodilators, corticosteroids and anti-interleukin 5 agents or combinations thereof.

Aspect 25) A method of treatment of eosinophilic airway inflammation in a subject, comprising the steps of:
  a) Determining whether the subject is in need of receiving eosinophilic airway inflammation treatment comprising performing the method according to any one of aspects 12 to 19; and
  b) Treating the subject diagnosed in step a) as being in need of eosinophilic airway inflammation treatment with a treatment selected from the group consisting of: macrolides, anti-leukotriene agents, bronchodilators, corticosteroids and anti-interleukin 5 agents or combinations thereof. Preferably treatment is selected from the group consisting of: bronchodilators, corticosteroids and anti-interleukin 5 agents or combinations thereof.

Aspect 26) A device for use in an in vitro method of diagnosing, prognosing and/or monitoring neutrophilic airway inflammation, or of discriminating neutrophilic airway inflammation from paucigranulocytic or eosinophilic airway inflammation, or of treatment of neutrophilic airway inflammation in a subject, said device comprising detection means for one or more VOCs selected from the group consisting of:
  3-tetradecene ($C_{14}H_{28}$),
  1-pentadecene ($C_{15}H_{30}$),
  3,7-dimethylnonane ($C_{11}H_{24}$),
  nonanal ($C_9H_{18}O$), and
  1-propanol ($C_3H_8O$), in a sample of exhaled breath from said subject.

Aspect 27) The device according to aspect 26, further comprising a processing unit, said processing unit receiving and processing signals obtained from said detection means.

Aspect 28) The device according to aspect 26 or 27, further comprising a breath collector.

Aspect 29) The device according to aspects 27 or 28, wherein said processing unit calculates the amount of the respective VOCs from the signal obtained from the detection means; compares said amount of said one or more VOCs with the respective one or more reference value(s) of said VOCs representing a known diagnosis, prognosis and/or monitoring status of neutrophilic airway inflammation; finds a deviation or no deviation of the amount of said one or more VOCs from said reference value; and attributes to said finding of deviation or no deviation a particular diagnosis, prognosis, and/or monitoring status of the neutrophilic airway inflammation in the subject.

Aspect 30) The device according to any one of aspects 26 to 29, wherein the detection means is selected from the group comprising: a metal oxide resistive sensor, an electrochemical sensor, an acoustic sensor, a holographic sensor, a conducting or composite polymer, an optical measurement system, a photo-ionization detector, a quartz crystal microbalances sensor, a thermal conductivity sensor, a bio-sensor and a sensor comprising carbon nanotubes.

Aspect 31) Use of the device according to any one of aspects 26 to 30 for diagnosing, prognosing and/or monitoring neutrophilic airway inflammation in a subject, preferably by performing the method according to any one of aspects 1 to 5, or for discriminating neutrophilic airway inflammation from paucigranulocytic airway inflammation, preferably by performing the method according to any one of aspects 6 to 8, or for discriminating neutrophilic airway inflammation from eosinophilic airway inflammation, preferably by performing the method according to any one of aspects 9 to 11, or for treatment of neutrophilic airway inflammation in a subject, preferably by performing the method according to any one of aspects 22 or 23.

Aspect 32) A device for use in an in vitro method of diagnosing, prognosing and/or monitoring eosinophilic airway inflammation, or of discriminating eosinophilic airway inflammation from paucigranulocytic airway inflammation, or of treatment of eosinophilic airway inflammation in a subject, said device comprising detection means for one or more VOCs selected from the group consisting of:
  2-hexanone ($C_6H_{12}O$), and
  hexane ($C_6H_{14}$),
  in a sample of exhaled breath from said subject.

Aspect 33) The device according to aspect 32, further comprising a processing unit, said processing unit receiving and processing signals from said detection means.

Aspect 34) The device according to aspect 32 or 33, further comprising a breath collector.

Aspect 35) The device according to aspects 33 or 34, wherein said processing unit calculates the amount of the respective VOCs from the signal obtained from the detection means; compares said amount of said one or more VOCs with the respective one or more reference value(s) of said VOCs representing a known diagnosis, prognosis and/or monitoring status of eosinophilic airway inflammation; finds a deviation or no deviation of the amount of said one or more VOCs from said reference value; and attributes to said finding of deviation or no deviation a particular diagnosis, prognosis, and/or monitoring status of the eosinophilic airway inflammation in the subject.

Aspect 36) The device according to any one of aspects 32 to 35, wherein the detection means is selected from the group comprising: a metal oxide resistive sensor, an electrochemical sensor, an acoustic sensor, a holographic sensor, a conducting or composite polymer, an optical measurement system, a photo-ionization detector, a quartz crystal microbalances sensor, a thermal conductivity sensor, a bio-sensor and a sensor comprising carbon nanotubes.

Aspect 37) Use of the device according to any one of aspects 32 to 36 for diagnosing, prognosing and/or monitoring eosinophilic airway inflammation in a subject, preferably by performing the method according to any one of aspects 12 to 16, or for discriminating eosinophilic airway inflammation from paucigranulocytic airway inflammation, preferably by performing the method according to any one of aspects 17 to 19, or for treatment of eosinophilic airway inflammation in a subject, preferably by performing the method according to any one of aspects 24 or 25.

Aspect 38) A system comprising:
  a computer data repository that comprises a reference value representing a known diagnosis, prognosis and/or monitoring status of said airway inflammation as defined herein; and
  a computer system programmed to access the data repository and to use information from the data repository and compare it to the information on the identity and quantity of VOCs in a sample of exhaled breath from a subject and to diagnose, prognose and/or monitor said airway systemic inflammatory condition as defined herein in the subject, based on said comparison. In one embodiment, said airway inflammation may be neutrophilic airway inflammation and said comparison may be done using the method according to any one of aspects 1 to 11. In another embodiment, said airway inflammation may be eosinophilic airway inflammation and said comparison may be done using the method according to any one of aspects 12 to 19.

Aspect 39) A method for making diagnosis, prognosis and/or monitoring of an airway inflammation in a subject comprising:

(i) Receiving data representative of identity and values of the amount of one or more VOCs present in a sample of exhaled breath from a subject;

(ii) Accessing a data repository on a computer, said data repository comprising a reference identity and a reference value of the amount of said one or more VOCs, said reference value of said one or more VOCs representing a known diagnosis, prognosis and/or monitoring status of an airway inflammation; and (iii) Comparing the data as received in (i) with the reference identity and value in the data repository on the computer, thereby diagnosing, prognosing and/or monitoring said airway inflammatory condition in the subject. In one embodiment, said airway inflammatory condition may be neutrophilic airway inflammation and said comparison may be done using the method according to any one of aspects 1 to 11. In another embodiment, said airway inflammatory condition may be eosinophilic airway inflammation and said comparison may be done using the method according to any one of aspects 12 to 19.

In certain embodiments of aspects 38 and 39, the determination of what action is to be taken, e.g., by a clinician, in view of said diagnosis, prediction and/or prognosis is performed by a (the) computer. In certain embodiments of aspects 38 and 39, a (the) computer reports (i.e., generates an electronic report of) the action to be taken, preferably substantially in real time.

BRIEF DESCRIPTION OF THE FIGURES

The present invention is illustrated by the following figures which are to be considered for illustrative purposes only and in no way limit the invention to the embodiments disclosed therein.

DETAILED DESCRIPTION OF THE INVENTION

Figure 1:
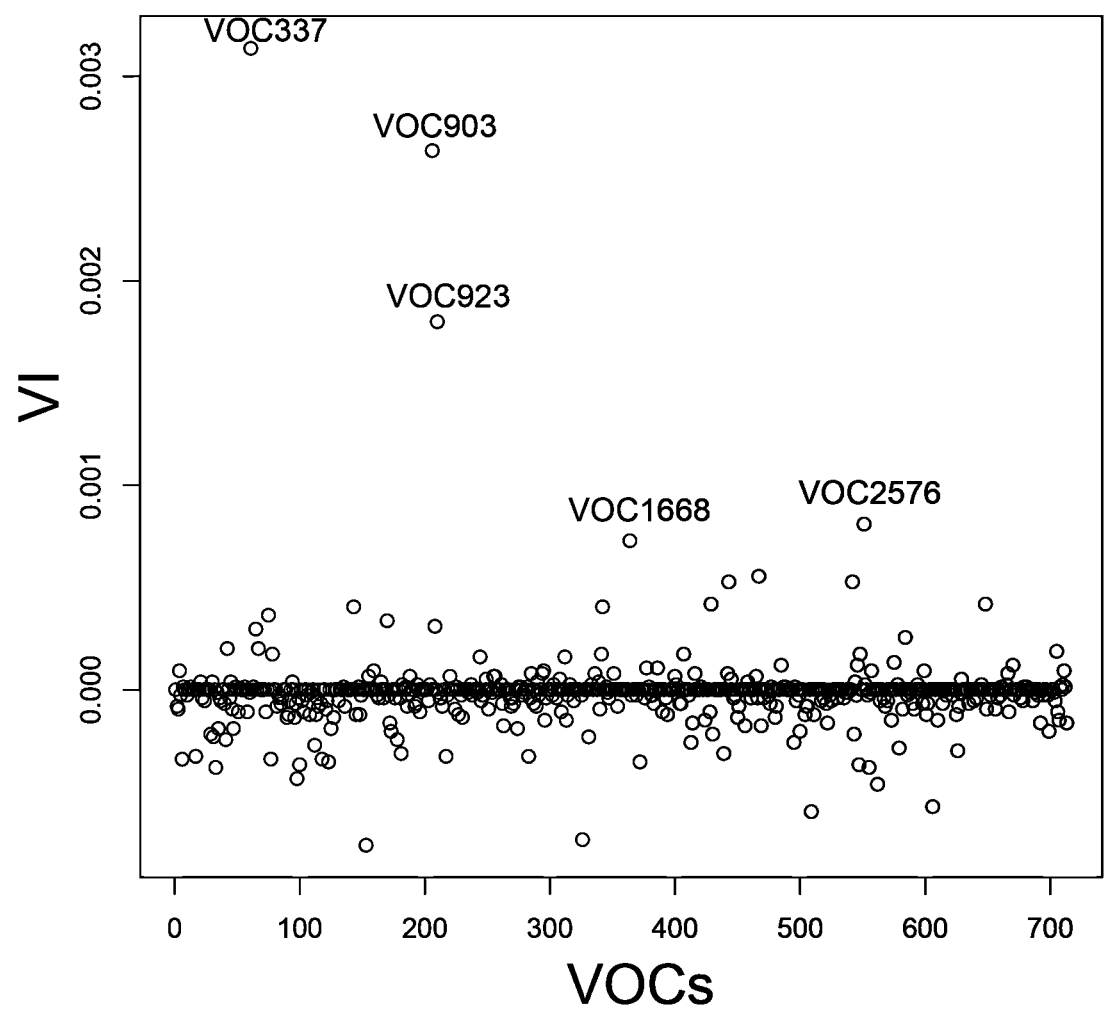
FIG. 1: represents the VI plot of VOCs. VOC 337 (hexane), VOC 903 (2-hexanone) and VOC 923 (undetermined) were deemed to be the best VOC-based discriminator between eosinophilic and paucigranulocytic asthma. VOC # is a consecutive compound number of the original data matrix referring to the column number. VOC 337 was deemed to be the most relevant reaching the highest VI. VI: permutation-based variable importance measure based on conditional inference framework—the higher, the better.

As used herein, the singular forms "a", "an", and "the" include both singular and plural referents unless the context clearly dictates otherwise. By way of example, "a sample" refers to one or more than one sample.

The terms "comprising", "comprises" and "comprised of" as used herein are synonymous with "including", "includes" or "containing", "contains", and are inclusive or open-ended and do not exclude additional, non-recited members, elements or method steps.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

According to one aspect, provided herein is an in vitro method of diagnosing, prognosing and/or monitoring neutrophilic or eosinophilic airway inflammation in a subject, comprising determining the amount of one or more volatile organic compounds (VOCs). The method comprises diagnosing or prognosing neutrophilic or eosinophilic airway inflammation in a subject who is at risk of developing neutrophilic or eosinophilic airway inflammation, a subject who is suspected of having neutrophilic or eosinophilic airway inflammation, or a subject who was already diagnosed with airway inflammation using common diagnostic tests available in the art. The present invention further provides a method of monitoring neutrophilic or eosinophilic airway inflammation in a subject. The term "monitoring" as used herein generally refers to the monitoring of neutrophilic or eosinophilic airway inflammation progression or regression over time (e.g. between two or more sample of exhaled breath from a subject, taken at different time intervals), preferably following treatment. Also encompassed by this term is the evaluation of treatment efficacy using the methods of the present invention.

The terms "diagnosing" or "diagnosis" generally refer to the process or act of recognizing, deciding on or concluding on a disease or condition in a subject on the basis of symptoms and signs and/or from results of various diagnostic procedures (such as, for example, from knowing the presence, absence and/or amount of one or more VOCs characteristic of the diagnosed disease or condition).

The terms "prognosing" or "prognosis" generally refer to anticipation on the progression of a disease or condition and the prospect (e.g., the probability, duration, and/or extent) of recovery. A good prognosis of the diseases or conditions may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions may generally encompass anticipation of a substandard recovery and/or unsatisfactorily slow recovery, or to substantially no recovery or even further worsening of such.

According to the present invention there are generally three subtypes of airway inflammation according to the type of inflammatory cells associated to, causing and/or underlying airway inflammation, referred to as neutrophilic, paucigranulocytic and eosinophilic airway inflammation. In the art, determination of the subtype of airway inflammation in a subject is carried out by counting inflammatory cells, for example using a heamocytometer, in induced sputum from said subject. By "sputum" is meant the mucoid matter contained in or discharged from the nasal or buccal cavity of a subject, including saliva and discharges from the respiratory passages, including the lungs. Methods for sputum induction are known in the art, such as hypertonic saline inhalation.

In the context of the present invention, "eosinophilic airway inflammation" refers to the presence of eosinophils in the airways, preferably a sputum eosinophils count greater than or equal to 3% of the total white cells present in the sputum. "Neutrophilic airway inflammation" refers to the presence of neutrophils in the airways, preferably a sputum neutrophils count greater than or equal to 70%, more preferably greater than or equal to 76%, of the total white cells present in the sputum. "Paucigranulocytic airway inflammation" refers to normal levels of eosinophils and neutrophils in the airways, i.e. absence or low levels of neutrophils and eosinophils in the airways, preferably a sputum eosinophils count lower than 3% and sputum neutrophils count lower than 76% of the total white cells present in the sputum.

The term "airway inflammation" refers to any disease or disorder that causes inflammation of the airways, including, but not limited to, asthma, chronic obstructive pulmonary disease (COPD), cystic fibrosis, emphysema, bronchitis, acute respiratory distress syndrome, bronchial constriction, coughing, phlegm, bronchial adenoma, pulmonary tuberculosis, pulmonary emphysema and lung abscess, or combinations thereof.

The term "subject" can be any mammal. Preferably the subject is a human. More preferably the subject is a human suffering from airway inflammation, such as, but not limited to, asthma, chronic obstructive pulmonary disease, cystic fibrosis, emphysema, bronchitis, acute respiratory distress syndrome, bronchial constriction, coughing, phlegm, bronchial adenoma, pulmonary tuberculosis, pulmonary emphysema and lung abscess, or combination thereof. Even more preferred subject is a human suffering from asthma.

The terms "amount", "quantity", or "level" are used herein interchangeably and are generally well understood in the art. The terms as used herein may particularly refer to an absolute quantification of a VOC in a sample, or to a relative quantification of a VOC in a sample, i.e., relative to another value such as relative to a reference value as taught herein, or to a range of values indicating a base-line expression of the VOCs. These values or ranges can be obtained from a single subject or from a group of subjects.

The term "volatile organic compounds" (abbreviated VOC, or VOCs) refers to organic chemicals, or derivatives thereof, present in exhaled breath from a subject. The VOCs of interest in the present application are incorporated in table 1 below as an example. The skilled person is well aware that VOCs may be referred to by different names, or synonyms.

TABLE 1

VOC descriptions and chemical composition

| VOCS | Synonym | Chemical formula |
|---|---|---|
| 3-tetradecene | | C14H28 |
| 1-pentadecene | pentadecene, pentadec-1-ene | C15H30 |
| 1-propanol | propan-1-ol | C3H8O |
| 3,7-dimethylnonane | | C11H24 |
| nonanal | nonanaldehyde, pelargonaldehyde | C9H18O |
| hexane | n-hexane | C6H14 |
| 2-hexanone | butyl methyl ketone, hexan-2-one | C6H12O |

A sample of exhaled breath may be obtained by collecting exhaled air from the subject, for example by requesting the subject to exhale air into a gas-sampling container, such as a bag, a bottle or any other suitable gas-sampling product. Preferably the gas-sampling container resists gas permeation both into and out of the bag and/or is chemically inert, thereby assuring sample integrity. Exhaled breath may also be collected using a breath collector apparatus. Preferably collection of a sample of exhaled breath is performed in a minimally invasive or a non-invasive manner.

The determination of the amount of one or more VOCs in a sample of exhaled breath from a subject may be performed by the use of at least one technique including, but not limited to, Gas-Chromatography (GC), Gas-Chromatography-lined Mass Spectrometry (GC/MS), Liquid Chromatography-tandem mass spectrometry (LC/MS), Ion Mobility Spectrometry/Mass Spectrometry (IMS/MS), Proton Transfer Reaction Mass-Spectrometry (PTR-MS), Electronic Nose device, quartz crystal microbalance or chemically sensitive sensors.

As shown in the examples below, the amount of one or more VOCs in a sample of exhaled breath from a subject may be determined using thermal desorption-gas chromatography-time of flight-mass spectrometry (GC-tof-MS). In certain embodiments, breath of the subject is collected in an inert bag, then the content of the bag is transported under standardised conditions onto desorption tubes and VOCs are analyzed by thermally desorbing the content of the tube and then separated by capillary gas chromatography. Then volatile organic peaks are detected with MS and identified using for example a library, such as the National Institute of Standards and Technology (NIST) library (available at http://www.nist.gov/srd/nistla.cfm). Thermal desorption may be performed at the GC inlet at a temperature of, e.g., about 200-350° C. In all chromatography, separation occurs when the sample mixture is introduced (injected) into a mobile phase. Gas chromatography (GC) typically uses an inert gas such as helium as the mobile phase. GC/MS allows for the separation, identification and/or quantification of individual components from a biological sample. MS methods which may be used with the present invention include, but are not limited to, electron ionization, electrospray ionization, glow discharge, field desorption (FD), fast atom bombardment (FAB), thermospray, desorption/ionization on silicon (DIOS), Direct Analysis in Real Time (DART), atmospheric pressure chemical ionization (APCI), secondary ion mass spectrometry (SIMS), spark ionization and thermal ionization (TIMS). Matrix assisted laser desorption ionization time-of-flight mass spectrometry (MALDI-TOF-MS) is an example of a mass spectroscopy method which may be used to determine one or more VOCs from a sample of exhaled breath from a subject.

In a preferred embodiment, the in vitro methods further comprise the steps of:
 a) Comparing said amount of one or more VOCs with a reference value, said reference value representing a known diagnosis, prognosis and/or monitoring status of neutrophilic or eosinophilic airway inflammation;
 b) Finding a deviation or no deviation of the amount of said one or more VOCs from said reference value; and
 c) Attributing said finding of deviation or no deviation to a particular diagnosis, prognosis and/or monitoring status of neutrophilic or eosinophilic airway inflammation in the subject.

In another preferred embodiment, the reference value is the amount of the same one or more VOCs in exhaled breath from a healthy subject and/or a subject suffering from a different subtype of airway inflammation than the subtype of airway inflammation to be diagnosed, prognosed or monitored. Preferably said different subtype of airway inflammation is paucigranulocytic airway inflammation, well-known in the art to be characterized by normal levels of eosinophils and neutrophils in the sputum, and hence having the same or nearly the same inflammatory characteristics than healthy subjects (Louis et al.: Induced Sputum—Towards Normal Values. Non Invasive Assessment of airways inflammation in asthma and COPD. 14th, tetrapoleos street, Athens, 115 27, Greece: Paschalidis Medical Publications; 2011: 113-123. ISBN 978-960-489-104-7 Chapter 7).

The term "healthy subject" refers to a subject not affected by airway inflammation, and preferably with no reported history of airway inflammation.

The term "deviation of the amount" refers either to elevated or reduced amounts of one or more VOCs of the invention in a sample of exhaled breath from a subject compared to a reference value. By "elevated amounts" we mean that the amount of said one or more VOCs in a sample of exhaled breath from a subject is statistically higher than the reference value. By "reduced amounts" we mean that the amount of said one or more VOCs in a sample of exhaled breath from a subject is statistically lower than the reference value. The amount may be considered to be statistically higher or lower if its value differs from a predetermined threshold value. This threshold value can, for example, be the median of the amount of VOCs determined in a sample of exhaled breath from a population of healthy subjects or subjects suffering from a different subtype of airway inflammation than the subtype of airway inflammation to be determined, prognosed or monitored, as shown in table 3.

The term "no deviation of the amount" refers to similar or unchanged amounts of one or more VOCs of the invention in a sample of exhaled breath from a subject compared to a reference value. By "similar or unchanged level" is meant that the difference of the amount of said one or more VOCs in a sample of exhaled breath from the subject compared to the reference value is not statistically significant.

Preferably, the reference value is obtained in samples of exhaled breath obtained from one or more subjects of the same species and the same sex and age group as the subject in which the subtype of airway inflammation is to be determined, prognosed or monitored.

Alternatively, the reference value may be a previous value for the amount of one or more VOCs obtained in a sample of exhaled breath from a specific subject. This kind of reference value may be used if the method is to be used for monitoring the subtype of airway inflammation in a subject, e.g. over time, or to monitor the response of a subject to a particular treatment.

Preferably, the reference value is the average amount of the same one or more VOCs found in samples of exhaled breath from a population of subjects. Preferably, said average expression level is determined once and then stored in a database for reference.

The present invention also provides methods of treatment of eosinophilic or neutrophilic airway inflammation in a subject, which phrase includes subjects that would benefit from treatment of a given condition, such as eosinophilic or neutrophilic airway inflammation. Such subjects may include, without limitation, those that are or have been diagnosed with said condition, those prone to develop said condition and/or those in whom said condition is to be prevented.

The terms "treatment" or "treating" encompasses both the therapeutic treatment of an already developed airway inflammation, such as neutrophilic or eosinophilic airway inflammation, as well as prophylactic or preventative measures, wherein the aim is to prevent or lessen the chances of incidence of airway inflammation. Beneficial or desired clinical results may include, without limitation, alleviation of one or more symptoms or one or more markers, such as, but not limited to, the VOCs according to the present invention, diminishment of extent of disease, stabilized (i.e., not worsening) state of disease, delay or slowing of disease progression, amelioration or palliation of the disease state, and the like. "Treatment" or "treating" can also mean prolonging survival as compared to expected survival if not receiving treatment.

Useful treatments of neutrophilic airway inflammation include, with no limitation, macrolides, anti-leukotriene agents and/or bronchodilators or combinations thereof.

Useful treatments of eosinophilic airway inflammation include, with no limitation, bronchodilators, corticosteroids and/or anti-interleukin 5 agents or combinations thereof.

The term "macrolides" refers to group of drugs whose activity stems from the presence of a macrolide ring, i.e. a large macrocyclic lactone ring to which one or more deoxy sugars, usually cladinose and desosamine, may be attached. Examples of macrolides include, but are not limited to, antibiotics (such as clarithromycin or ketolides), non-antibiotics (such as immunosuppressants or immunomodulators, for example tacrolimus), or antifungal drugs (such as amphotericin B).

The term "anti-leukotriene agents" refers to compounds which oppose the function of leukotriene. Non-limiting examples include leukotriene related enzyme inhibitors (such as 5-lipoxygenase inhibitors, like meclofenamate sodium) or leukotriene receptor antagonists (such as montelukast).

The term "bronchodilators" refers to substances that dilate the bronchi and/or bronchioles, thereby decreasing resistance in the respiratory airway and increasing airflow to the lungs. Examples of bronchodilators include, but are not limited to, short-acting β2-agonists (such as salbutamol), long-acting β2-agonists (such as salmeterol) or anticholinergics (such as tiotropium).

The term "corticosteroids" refers to a class of chemicals that includes the steroid hormones that are produced in the adrenal cortex of vertebrates or synthetic analogues thereof. Preferably corticosteroids are nebulized or inhaled in case or airway inflammation. Non-limiting examples of corticosteroids are methylprednisolone, beclomethasone or budesonide.

The term "anti-interleukin 5 agents" refers to compounds which oppose the function of interleukin-5 (IL-5) or IL-5 receptor. Non-limiting examples include antibodies against IL-5 (such as mepolizumab or reslizumab) or against IL-5 receptor (such as benralizumab).

The above treatments will be formulated for administration by manners known in the art acceptable for administration to a subject, preferably a human. The treatments can be administered directly into a tissue by injection or into a blood vessel supplying the tissue of interest. The treatments may also be administered "locoregionally", i.e., intravesically, intralesionally, and/or topically. The treatments may also be administered systemically by injection, inhalation, nebulization, suppository, transdermal delivery, etc.

In order to administer treatments described above, it will be appreciated that suitable carriers, excipients, and other agents may be incorporated with active ingredients to provide improved transfer, delivery, tolerance, and the like. The skilled person is well aware that precise nature of the carrier or excipient or other material will depend on the route of administration. For example, the treatment may be orally administered, inhaled or injected. For general principles in airway inflammation treatment, the reader is referred to international European Respiratory Society and American Thoracic Society guidelines (Chung et al, Eur Respir J. 2014; 43(2): 343-73).

One skilled in the art can also easily determine the appropriate dose, schedule, and method of administration for the treatment being used, in order to achieve the desired effect in the subject.

In another aspect, the invention provides a device for use in the methods according to the invention, said device comprising detection means for one or more VOCs in a sample of exhaled breath from a subject.

Non limiting examples of detection means are metal oxide resistive sensors, electrochemical sensors (e.g. through an oxidation/reduction reaction of the target VOCs on working electrodes), resistive/capacitive/frequency measurement of conducting or composite polymers, optical measurement using e.g. infra-red (e.g. LED or some other IR-source, light filter with a photodetector) or UV light, photo-ionization detectors, frequency measurement quartz crystal microbalances/shear horizontal surface acoustic wave sensors, thermal measurement techniques using thermal conductivity sensors, bio-sensors (e.g. an enzyme or protein attached to a secondary transducer), holographic sensors or sensors comprising carbon nanotubes.

In a preferred embodiment, the device further comprises a processing unit, said processing unit receiving and processing signals obtained from said detection means. Preferably, the processing unit comprises a learning and pattern recognition analyzer, wherein the learning and pattern recognition analyzer receives detection means signals and analyses them by various pattern analysis algorithms to produce an output signal. By comparing the output signal for said one or more VOCs within the exhaled breath of the subject with a database of stored or known reference value(s) of said one or more VOCs, the type of exhaled VOCs can be identified and its concentration can be measured. Non limiting examples of learning and pattern recognition algorithms are artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. In addition, said processing unit can compare the concentration of said one- or more VOCs to a known concentration of said one or more VOCs in a reference sample, in order to correlate the VOCs profile in the exhaled breath sample of the subject to a known diagnostic VOCs profile, e.g. according to the method of the invention as described herein.

In another preferred embodiment, the device of the present invention further comprises a breath collector. The breath collector may further be used to increase detection means sensitivity either by concentrating the breath VOCs to be detected or by dehumidifying the subject's breath prior to analyzing. This allows for increased resolution in discriminating between different breath samples.

Breath concentrators that are within the scope of the present invention include, but are not limited to, solid phase micro extraction (SPME), sorbent tubes or cryogenic condensates.

Examples of dehumidifiers include, but are not limited to, devices that draw moist air over cold refrigerated coils, silica gel, activated carbon or desiccant molecular sieves.

The present invention is further illustrated by the following examples, which do not limit the scope of the invention in any way.

EXAMPLES

Methods

Subject Characteristics and Study Design

We conducted a prospective study on 276 asthmatics recruited from the University asthma clinic of Liege (Belgium) between Oct. 8, 2010 and January 2014. The recruitment of asthmatics stopped when eosinophilic, paucigranulocytic and neutrophilic subtypes reached at least 50 asthmatics in each group. The mixed granulocytic asthmatics were quite rare so we decided not to include them in the statistical analysis.

Patients attended the clinic on 2 days at a one-week interval. Patients who had a history of upper or lower respiratory tract infection during the 4 weeks before to the measurements were excluded from the study. On day 1 each patient underwent VOCs measurement, FENO (exhaled nitric oxide) measurement, spirometry with bronchodilation, sputum induction, gave a blood sample and filled in validated asthma control and quality of life questionnaires. Informed consent was also obtained. On day 2 the subjects underwent methacholine challenge after refraining from using bronchodilators for the appropriate time (8 hours for short acting and 24 h for long acting bronchodilators) as long as the baseline forced expiratory volume in 1s ($FEV_1$) value was not less than 70% predicted.

Asthma was diagnosed based on symptoms of cough, breathlessness or dyspnea together with the demonstration of airflow variability. The latter was defined by airway hyper-responsiveness demonstrated by one or more of the following: increase in $FEV_1$ of ≥12% and 200 ml following inhalation of 400 µg of salbutamol or inhaled concentration of methacholine provoking a 20% fall in $FEV_1$ of less than 16 mg/ml. Methacholine challenges were performed according to a standardized methodology as previously described. Subjects were characterized as atopic if they had at least one positive specific IgE (>0.35 KU/L; Phadia) for at least one common aeroallergens (cat, dog, house dust mites, grass pollen, tree pollen and a mixture of moulds). Quality of life was assessed using the self-administered Asthma Quality of Life Questionnaire (AQLQ) and asthma control by the Juniper ACQ. The report of the study was approved by the Ethics Committee of CHU Liege (Belgium).

Patients were classified in four asthma inflammatory subtypes according to the results of their sputum cell count. Patients were defined as eosinophilic (≥3% eosinophils in the sputum), neutrophilic (≥76% neutrophils), mixed granulocytic (≥3% eosinophils and ≥76% neutrophils) and paucigranulocytic asthma (<3% eosinophils and <76% neutrophils).

VOCs Collection and Analysis

All breath samples were donated between 9 and 11 a.m. in the same room, to minimize the effect of variation in background air. Exhaled air was collected by exhaling into inert Tedlar bags (5 L). Subjects were asked to inhale, hold their breath for 5 seconds and subsequently fully exhale into the Tedlar bag. All Tedlar bags were washed twice with high-grade nitrogen as described by the manufacturer before usage to make sure all contaminants were eliminated. The content of the Tedlar bag was transported under standardised conditions onto desorption tubes (stainless steel two-bed sorption tubes, filled with carbograph 1TD/Carbopack X). These desorption tubes were placed inside the thermal desorption unit and quickly heated to 270° C. in order to release all VOCs and transport the released VOCs onto the GC-capillary. The used desorption unit was highly suitable for repeated, quantitative and reproducible measurements. Ten percent of the sample was injected into the GC, the remaining 90% transported to another adsorption tube for storage and may be used for later reanalysis. Just before the sample enters the GC, it is trapped by a cold trap at 5 degrees Celsius in order to concentrate the sample. Next, VOCs were separated by capillary gas chromatography (column: RTX-5 ms, 30 m×0.25 mm 5% diphenyl, 95% dimethylsiloxane, film thickness 1.0 µm, Thermo Electron Trace GC Ultra, Thermo Electron Corporation, Waltham, USA). The temperature of the chromatograph was programmed as follows: 40° C. during 5 minutes, then raised with 10° C./min until a final maximum temperature of 270° C. in the final step, this temperature was maintained for 5 min. Time-of-flight mass spectrometry was used to detect and identify components available in the samples. Electron ionisation mode was set at 70 eV and the mass range m/z 35-350 was measured. Sample frequency of the mass spectrometer was set to 5 Hz and analysis run time to 33 minutes.

Exhaled NO Measurement

FENO was measured by chemiluminescence using a nitric oxide monitor set at an exhalation flow rate of 50 ml/sec according to the ERS/ATS recommendations (NIOX, Aerocrine, Sweden). FENO was measured prior to measurement lung function tests, salbutamol administration and induced sputum.

Sputum Induction and Processing

Sputum was induced and processed as previously reported. Saline was inhaled through an ultrasonic nebulizer (Devilbiss 2000), the mean output of which was calculated to be 0.93 ml/min. The cup of the nebulizer was filled with 50 ml hypertonic/isotonic saline to which was added 1.75 ml salbutamol solution at 5 mg/ml. The dose of nebulized salbutamol was dependent on the duration of sputum induction and was calculated by multiplying the concentration of salbutamol in the cup of the nebulizer (169 mg/ml) by the output of the nebulizer (0.93 ml/min) and the duration of the induction. FEV1 was measured at 1, 3, 5, and 10 minutes after starting inhalation. Inhalation of saline was stopped after 10 minutes or when a fall in FEV1 of 20% from baseline had occurred. After performing spirometric measurements at 5 and 10 minutes the subjects were asked to rinse their mouth with tap water and to cough up sputum into a plastic container. For safety reasons, FEV1 was measured 10 and 20 minutes after the end of the induction in every patient. Subjects who still had a fall in FEV1 of 0.20% at this time received additional nebulized salbutamol and ipratropium bromide and were kept under observation until their FEV1 value had returned to within 5% of baseline.

Samples were poured into a 50 ml polypropylene tube, weighed, and diluted with a threefold weight of a phosphate buffered saline (PBS) solution for homogenization. The samples were then rocked at room temperature for 20 minutes and centrifuged at 400 g for 10 minutes at 4° C. The supernatant was stored at −80° C. until biochemical analyses for albumin and histamine. The cellular phase was dispersed in 1 ml PBS without Ca2+ and Mg2+ solution for total cell counts using a manual haemocytometer. The differential cell count was performed on cytospins stained with Diff-Quick by counting 500 cells under a light microscope.

Statistical Analysis

The results were expressed as mean±SD for continuous variables; median and interquartile ranges (IQR) were preferred for skewed distributions. For categorical variables, the number of observations and percentages were given in each category. Comparisons between different subtypes were performed with a Kruskal-Wallis test. The Spearman correlation coefficient was used to measure the association between clinical parameters. The receiver-operating characteristic (ROC) curve was constructed to determine cut-offs for variables in order to distinguish between various subtypes. Logistic regression analysis was used to assess the relationship between binary outcomes and sets of covariates, individually or in combination. We established formula taking into account independent predictors to predict the probability of inflammatory subtypes. The validity of the equations was tested in independent populations. The agreement between predicted and observed value was tested by Cohen Kappa's coefficient. Calculations were done using SAS version 9.1 (SAS Institute, Cary, N.C., USA). The results were considered to be significant at the 5% critical level ($p<0.05$).

To identify volatile organic compounds (VOCs) from the exhaled air able to discriminate between three asthma inflammatory subtypes (paucigranulocytic, eosinophilic and neutrophilic asthma), we used conditional Inference Forests (CIFs) to build an ensemble of conditional inference trees and to rank features based on the ability of components to predict asthma inflammatory subtype. The advantage of CIF framework is that the node variable selection and its posterior splitting are two separate steps. The CIFs do not show bias towards variables with many possible splits and are scale-independent due to association measure with statistical significance. Thus CIFs implemented in party and party-kit packages in R had been shown to provide a superior performance compared to traditional classification and regression trees (CART) including the widely used Random Forests by Breiman. Briefly, the aim of the CIFs in this study was to find the components with the strongest association to the inflammatory subtype in each of the three tested scenarios including eosinophilic/neutrophilic, eosinophilic/paucigranulocytic and neutrophilic/paucigranulocytic. The association of a particular compound to asthma inflammatory subtype via CIFs allowed identifying only compounds that are deemed to be associated to specific subtype, but did not provide enough information to form a robust classifier. In order to extract further information and to see the direction of each compound impact on the asthma sub-type, we had conducted Student's t-test on the amounts of the top ranked compounds (i.e. VOCs) from CIFs analysis. The original data consisted of 276 asthmatics and 3327 compounds with 122 patients exhibiting eosinophilic asthma, 50 with neutrophilic asthma, 14 with mixed granulocytic asthma and 90 with paucigranulocytic asthma. In order to improve power and reduce dimensionality of the dataset, we had filtered out the compounds that had <30 samples (i.e. the mixed granulocytic group was not analyzed). After filtering the eosinophilic/neutrophilic subset contained 172 samples and 561 compounds, the neutrophilic/paucigranulocytic subset contained 140 samples and 429 compounds, and the eosinophilic/paucigranulocytic subset contained 212 samples and 714 compounds. The parameters to build Conditional Inference Forests included $c_{quad}$ test statistic (teststat="quad"), multiple-testing correction via Monte Carlo resampling (testtype="MonteCarlo", nresample=9999), 65% of the dataset was used to build trees and the remaining one to calculate variable importance (fraction=0.65), the minimum criteria to continue splitting the tree node was set at p-value ≤0.01 (mincriterion=0.99), a minimum of 30 samples in a node were required to execute split (minsplit=30), a total of 999 trees were built (ntree=999), all predictor variables/compounds had a chance to be assigned to a tree node (mtry=0), the CI trees could have unlimited number of levels (maxdepth=0). The variable importance was calculated using the default settings of the varimp function. The importance of the variable/compound was measured via the standard decrease in MSE ("% IncMSE") measure. The statistical significance of the compounds identified across two asthma subgroups was calculated with the Student's t-test assuming different compound amounts variances in two groups.

We constructed ROC and PR curves using the conditional inference forest that we generated for VOCs selection, to evaluate the classification performance of the selected VOCs in the prediction of asthma subtypes. The performance of the ROC (AUROC) must be higher than 0.50 to be significant. We used the first 75% of patients dataset for training set and last 25% included patients for validation set. We tested various combinations of VOCs separately and in combination to find out the best potential classifier.

The study was conducted with the approval of the ethics committee of CHU Liege B70720096732, reference Liege 2009/161.

Results

All subjects were adults without any other acute or chronic disease than asthma. 276 asthmatics were sampled with 3327 volatile organic compounds detected. From those patients, 122 exhibited eosinophilic asthma, 90 had paucigranulocytic asthma, 50 neutrophilic asthma and 14 mixed granulocytic asthma. Their demographic functional and inflammatory characteristics are summarized in Table 2.

TABLE 2

Demographic and functional characteristics of 276 asthmatics recruited for the VOCs study.

| Characteristics | |
| --- | --- |
| N. | 276 |
| Age (yrs) | 50 ± 15 |
| Gender (% of female) | 59 |
| Smokers (%) | 18.5 |
| Ex-smokers (%) | 36 |
| Non-smokers (%) | 45.5 |
| $FEV_1$ (% pred) | 82 (24-133) |

Time-of-flight mass spectrometry was used to identify components (peaks) available in the samples.

When comparing volatile organic compounds present in the exhaled air of paucigranulocytic to those present in eosinophilic asthmatics, 3 components (VOC 337, VOC 903 and VOC 923, FIG. 1) were shown to be good discriminators. The chemical nature of these 3 compounds was identified using the NIST Library.

Figure 2:
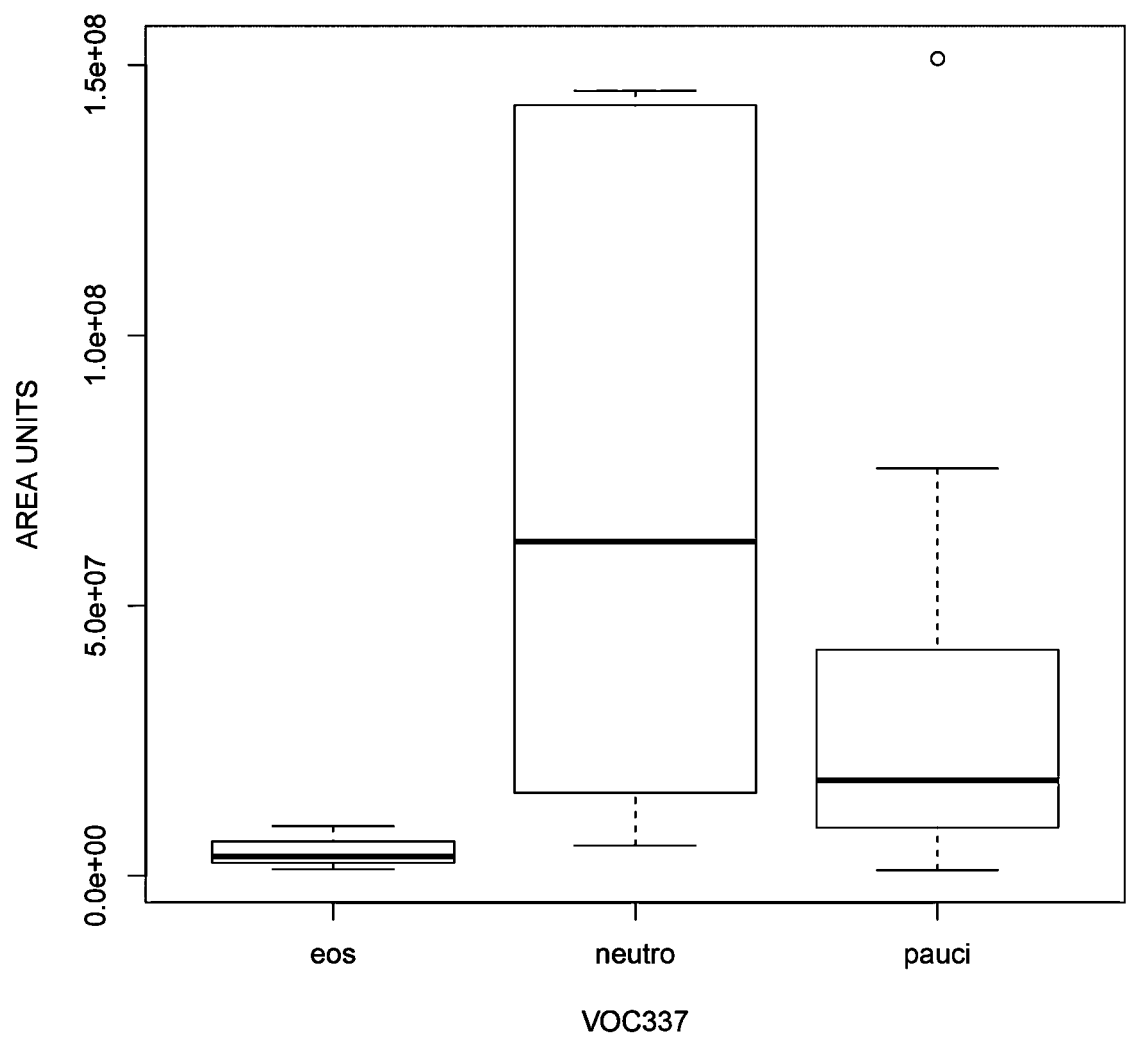
FIG. 2: represents the boxplot of VOC 337 (hexane) relative abundances. The medians are indicated by the black line. VI: variable importance.
Figure 3:
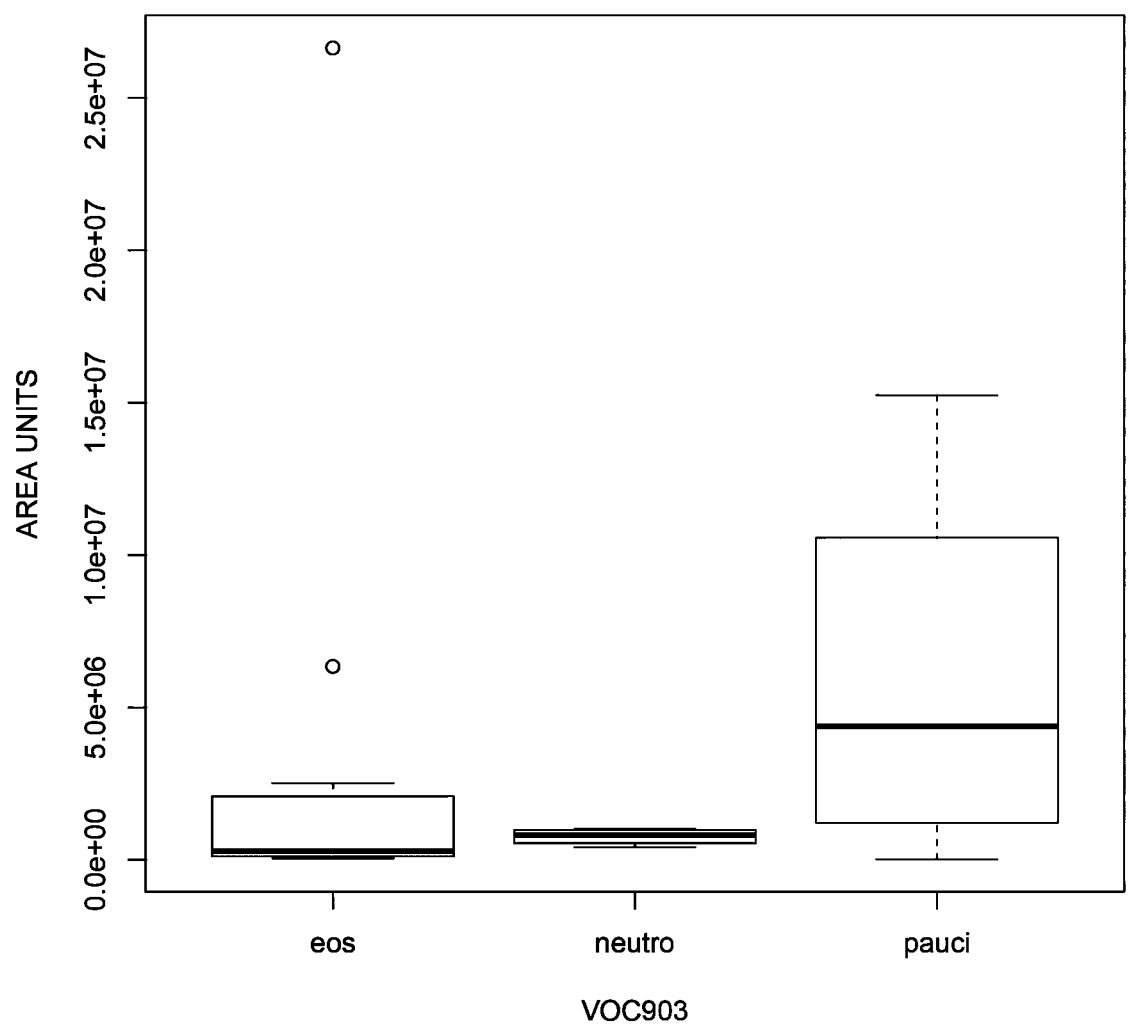
FIG. 3: represents the boxplot of VOC 903 (2-hexanone) relative abundances. The medians are indicated by the black line. VI: variable importance.
Figure 4:
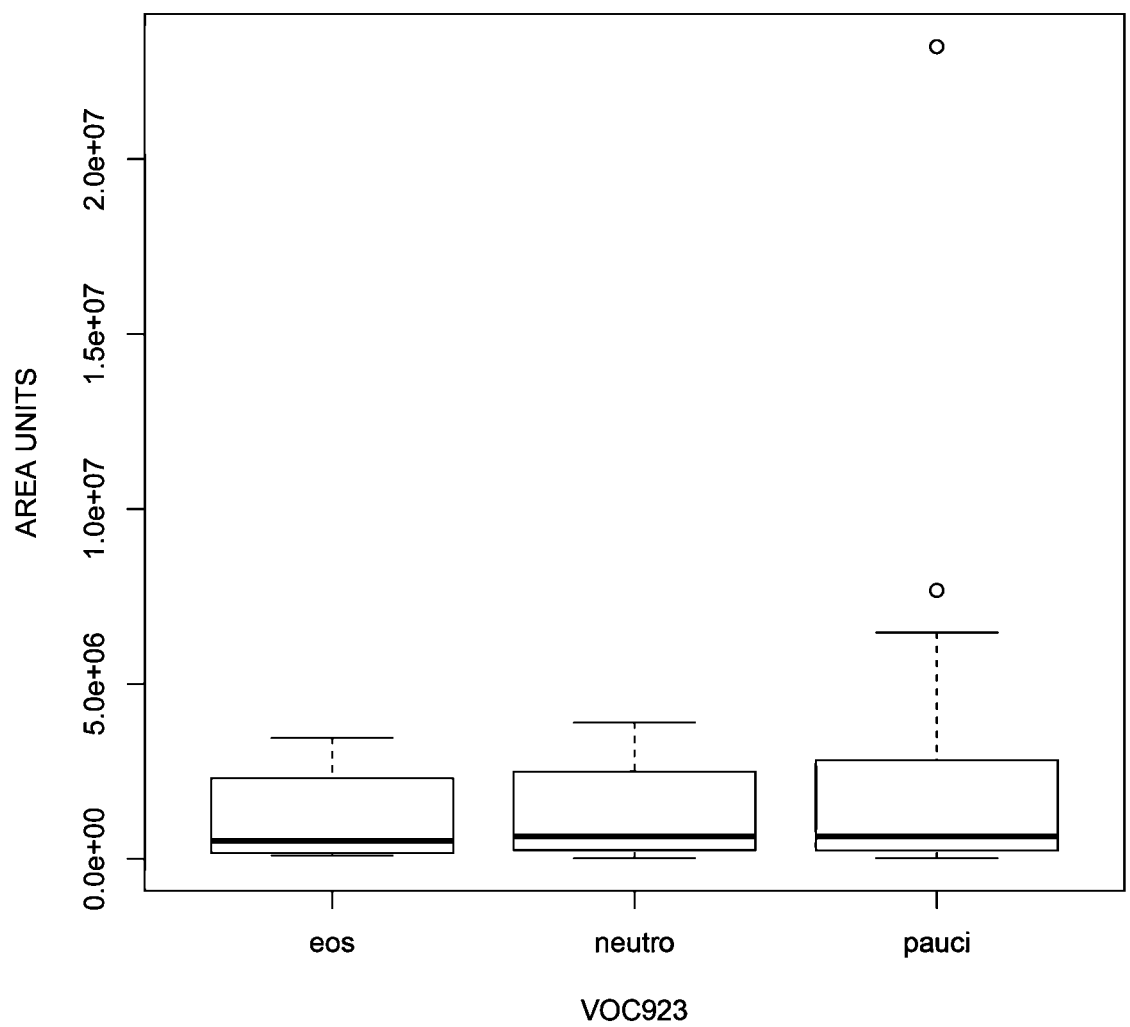
FIG. 4: represents the boxplot of VOC 923 relative abundances across different asthma inflammatory subtypes. The medians are indicated by the black line. VI: variable importance.

VOC 337 was shown to be hexane while VOC 903 was identified as 2-hexanone. VOC 923 remained undetermined. A possible explanation could be that this compound is not in the NIST Library or that the initial compound structure has been modified during heating of the tube and is no longer recognizable. On average hexane (VOC 337) was 5× more abundant in paucigranulocytic as compared to eosinophilic subtypes (FIG. 2, table 3). The same goes to discovery probability that was higher in paucigranulocytic group. The average area under the peak of 2-hexanone (VOC 903) was 15.5 times higher in paucigranulocytic as compared to eosinophilic group (FIG. 3, table 3). VOC923 levels were 1.2 times higher in paucigranulocytic asthma than in eosinophilic asthma (FIG. 4, table 3).

Figure 5:
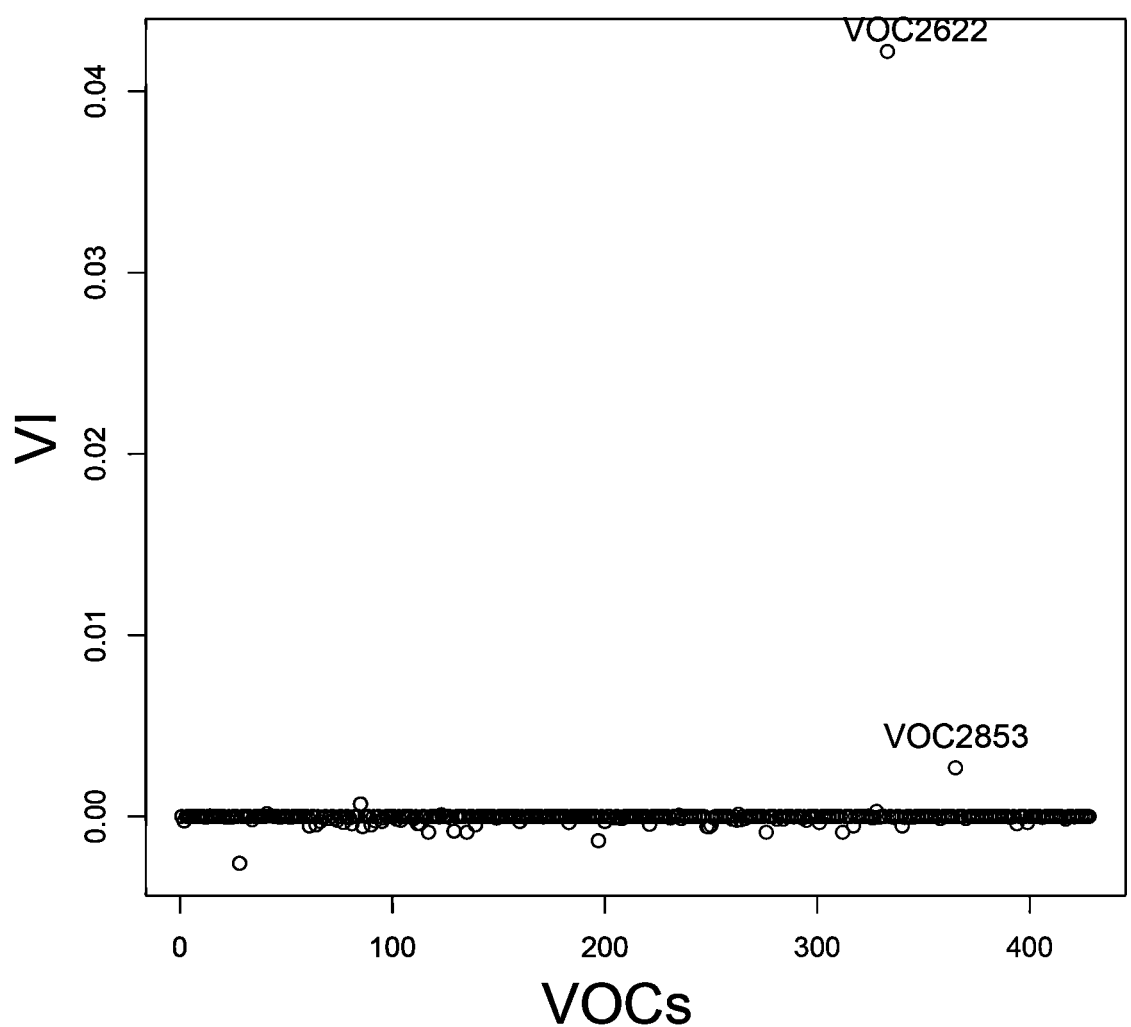
FIG. 5: represents the VI plot of VOCs showing the two peaks (VOC2622 and VOC2853) associated with the highest discriminant power between neutrophilic and paucigranulocytic asthma. VOC # is a consecutive compound number of the original data matrix referring to the column number. VI: variable importance.

We further compared the volatile organic compounds presents in the exhaled air of neutrophilic and paucigranulocytic asthmatics to identify discriminative VOCs associated with the neutrophilic subtype. We found that VOC 2622 and VOC 2853 were volatile organic compounds able to distinguish asthmatics with increased neutrophil counts as compared to paucigranulocytic asthma (FIG. 5).

Figure 6:
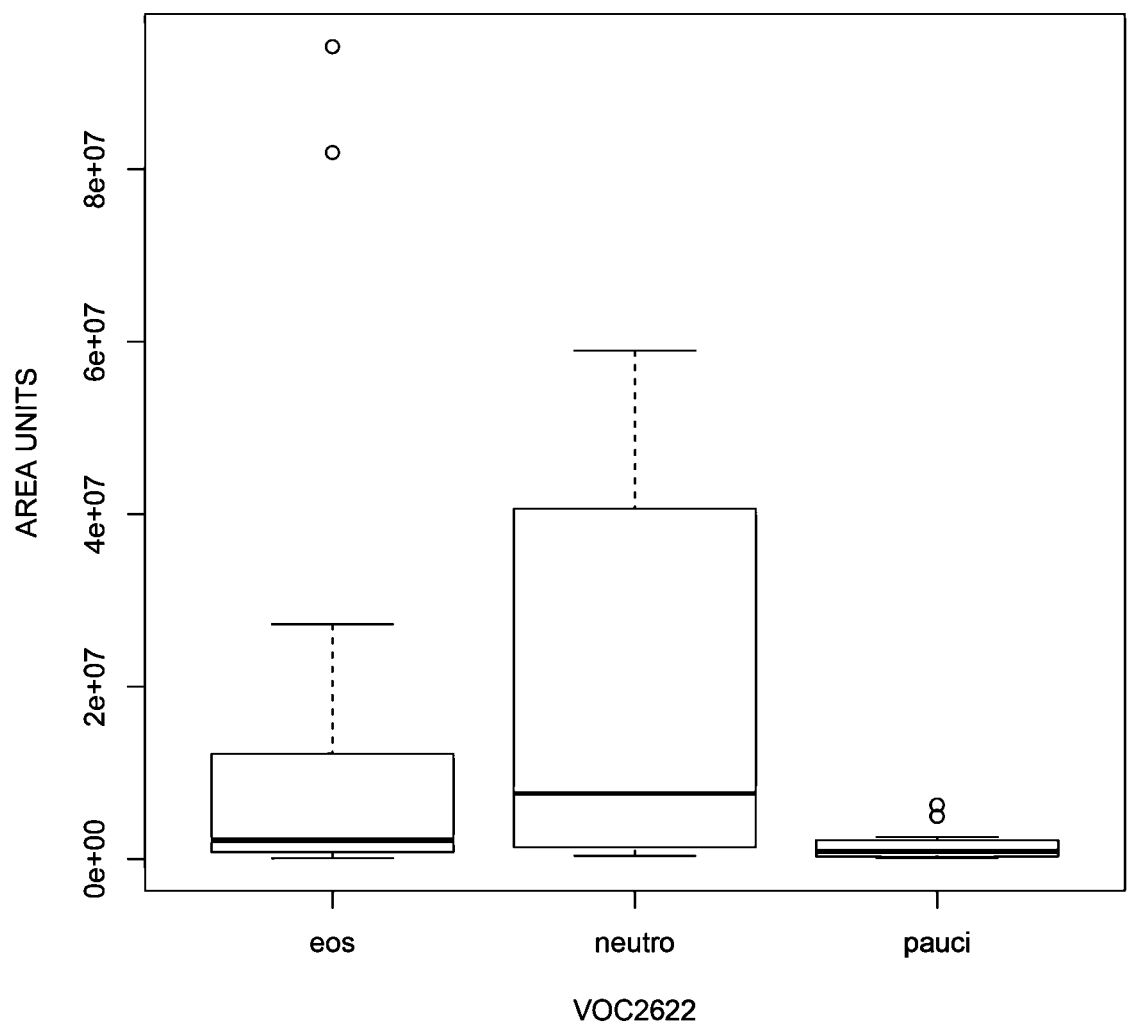
FIG. 6: represents the boxplot of VOC 2622 (3-tetradecene) relative abundances across different asthma inflammatory subtypes with black line representing median.
Figure 7:
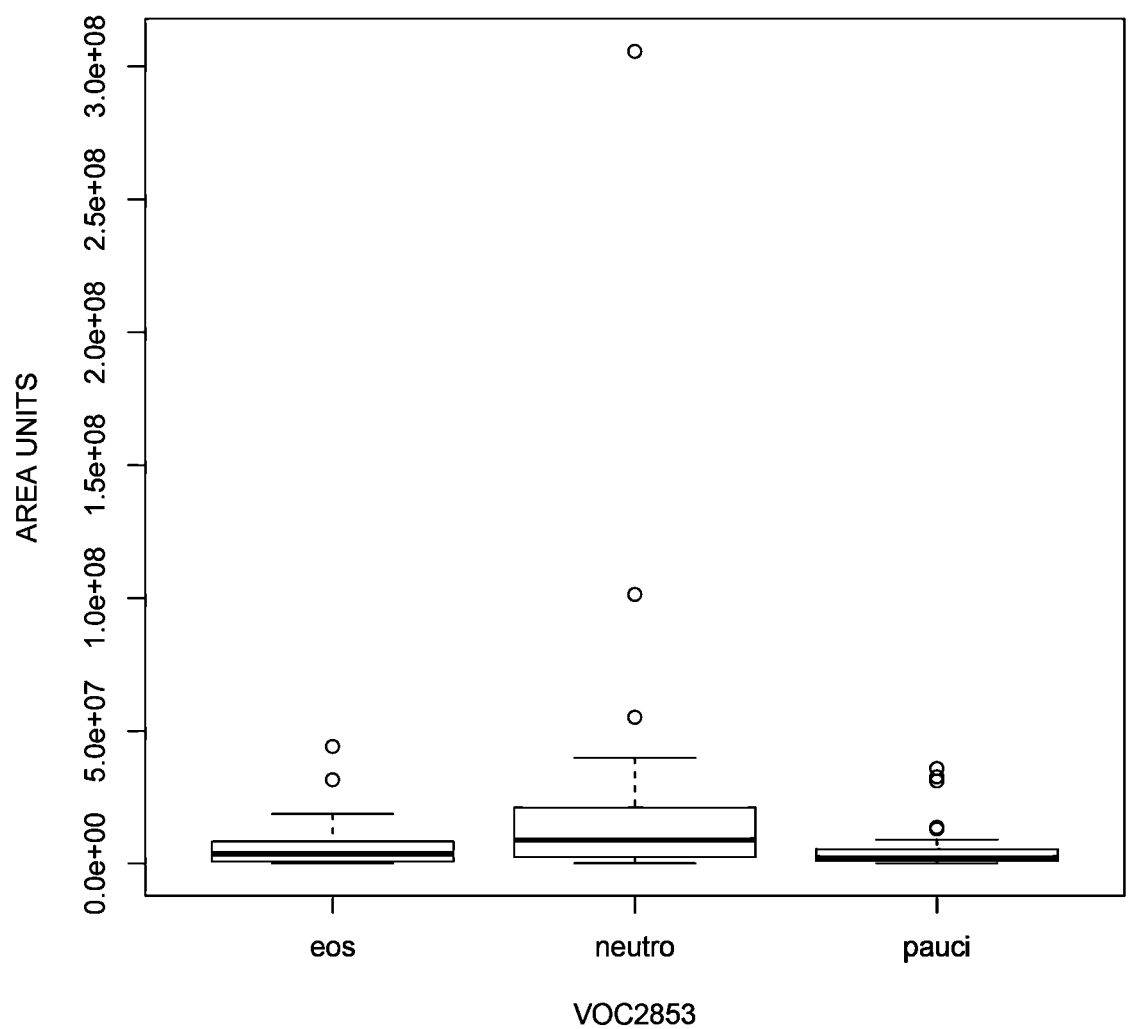
FIG. 7: represents the boxplot of VOC 2853 (1-pentadecene) relative abundances across different asthma inflammatory subtypes with black line representing median.

Using NIST library, we found that VOC 2622 was 3-tetradecene and VOC 2853 was 1-pentadecene (C15H30). 3-tetradecene was more abundant (8.8 times) in neutrophilic asthma than in paucigranulocytic subgroup (FIG. 6, table 3). The probability of detecting 3-tetradecene in neutrophilic asthma was 0.32 versus 0.144 in paucigranulocytic asthma. 3-tetradecene is not only more abundant but also occurs more frequently in neutrophilic subgroup. 1-pentadecen was also present at higher average concentration (4.3 times) and at higher probability of detection in neutrophilic asthmatics as compared to paucigranulocytic (FIG. 7, table 3).

Figure 8:
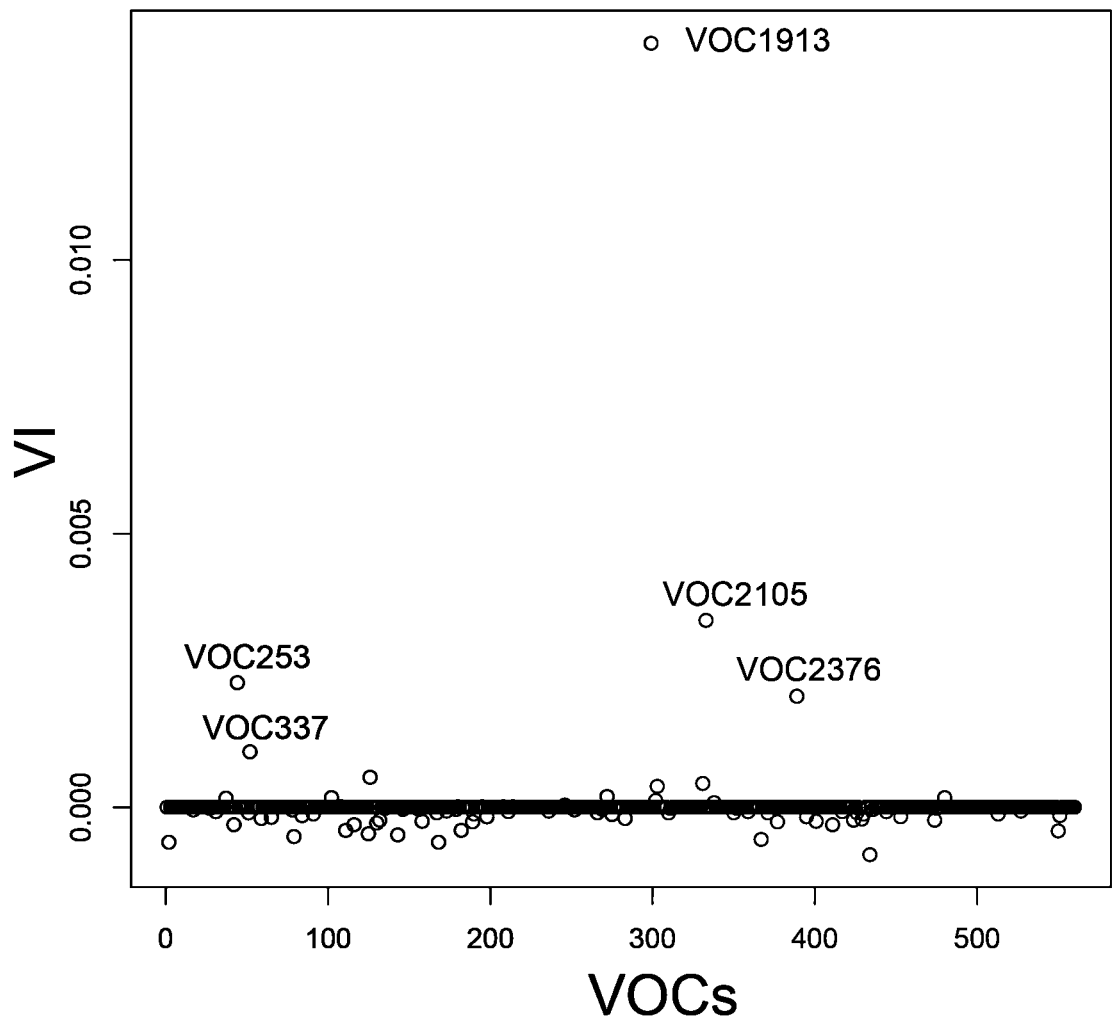
FIG. 8: represents the VI plot of VOCs showing VOC 1913 (3,7-dimethylnonane), VOC 2105 (nonanal) and VOC 253 (1-propanol) with the highest discriminative power between eosinophilic and neutrophilic asthma. VOC # is a consecutive compound number of the original data matrix referring to the column number. VI: variable importance.
Figure 9:
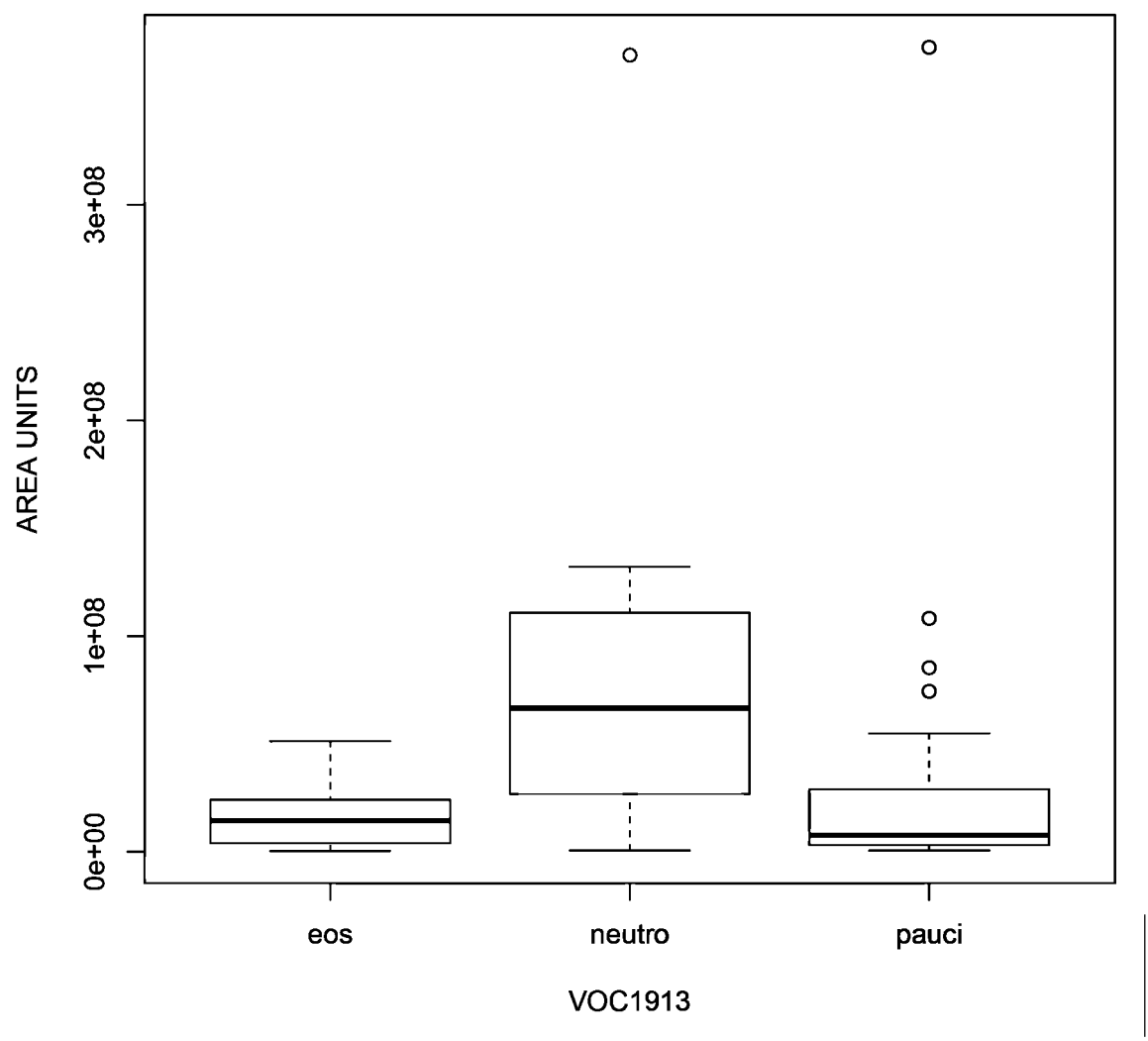
FIG. 9: represents the boxplot of VOC 1913 (3,7 dimethylnonane) relative abundances across different asthma inflammatory subtypes with black line representing median.
Figure 10:
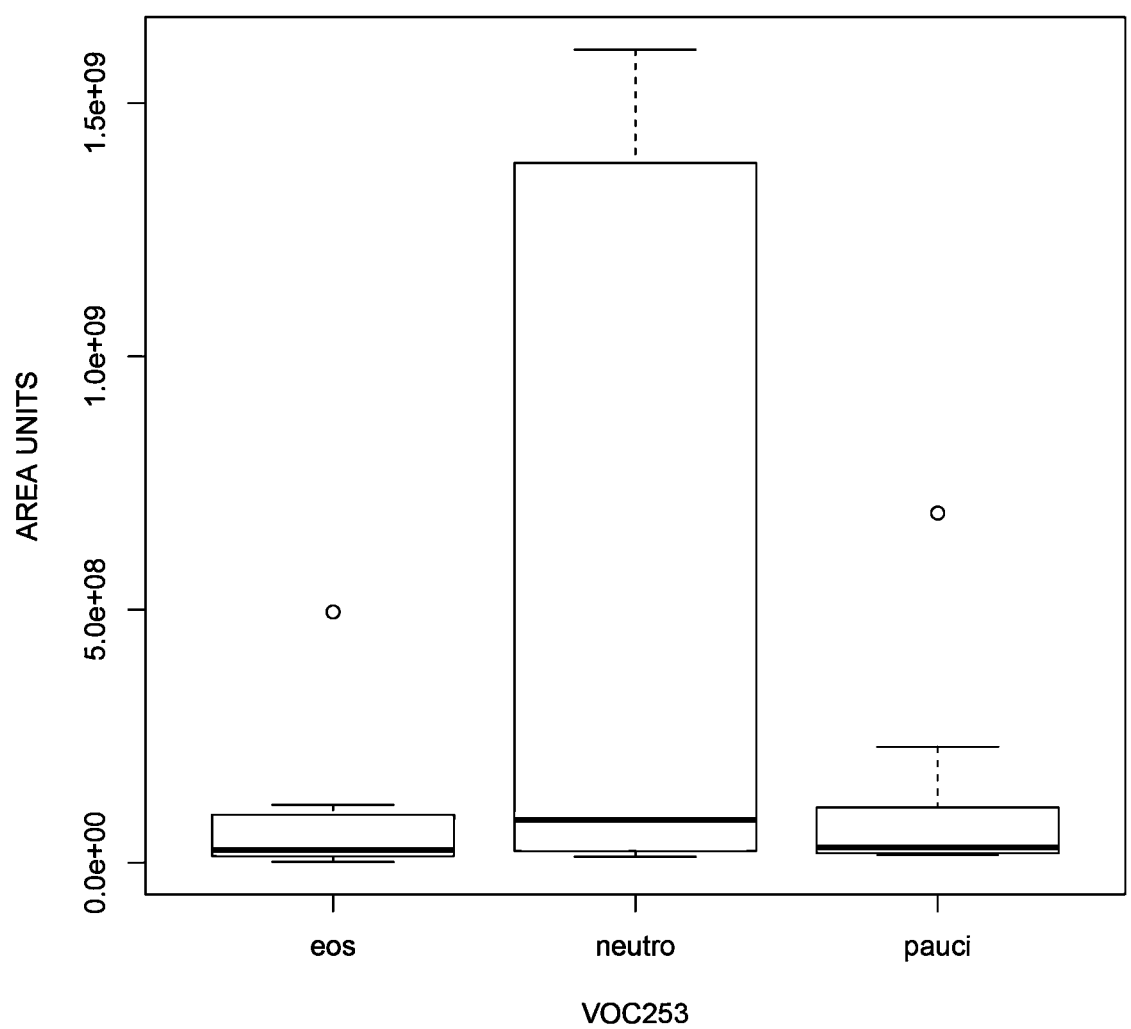
FIG. 10: represents the boxplot of VOC 253 relative abundances across different asthma inflammatory subtypes with black line representing median.

We tested the ability of VOCs to discriminate between eosinophilic and neutrophilic asthma. We showed that VOC 1913, VOC 2105 and VOC 253 were able to discriminate between eosinophilic and neutrophilic airway inflammation (FIG. 8). VOC 1913 was identified as 3,7-dimethylnonane in NIST library, while VOC 2105 and VOC 253 were found to be nonanal and 1-propanol, respectively. For this group actually the best-ranked VOCs were 3,7-dimethylnonane and nonanal followed by 1-propanol. The levels of 3,7-dimethylnonane were on average higher in neutrophilic subtypes (4.6 times) (FIG. 9, table 3). In the same line, 1-propanol was 3.4 more abundant in neutrophilic subtype (FIG. 10, table 3).

Figure 11:
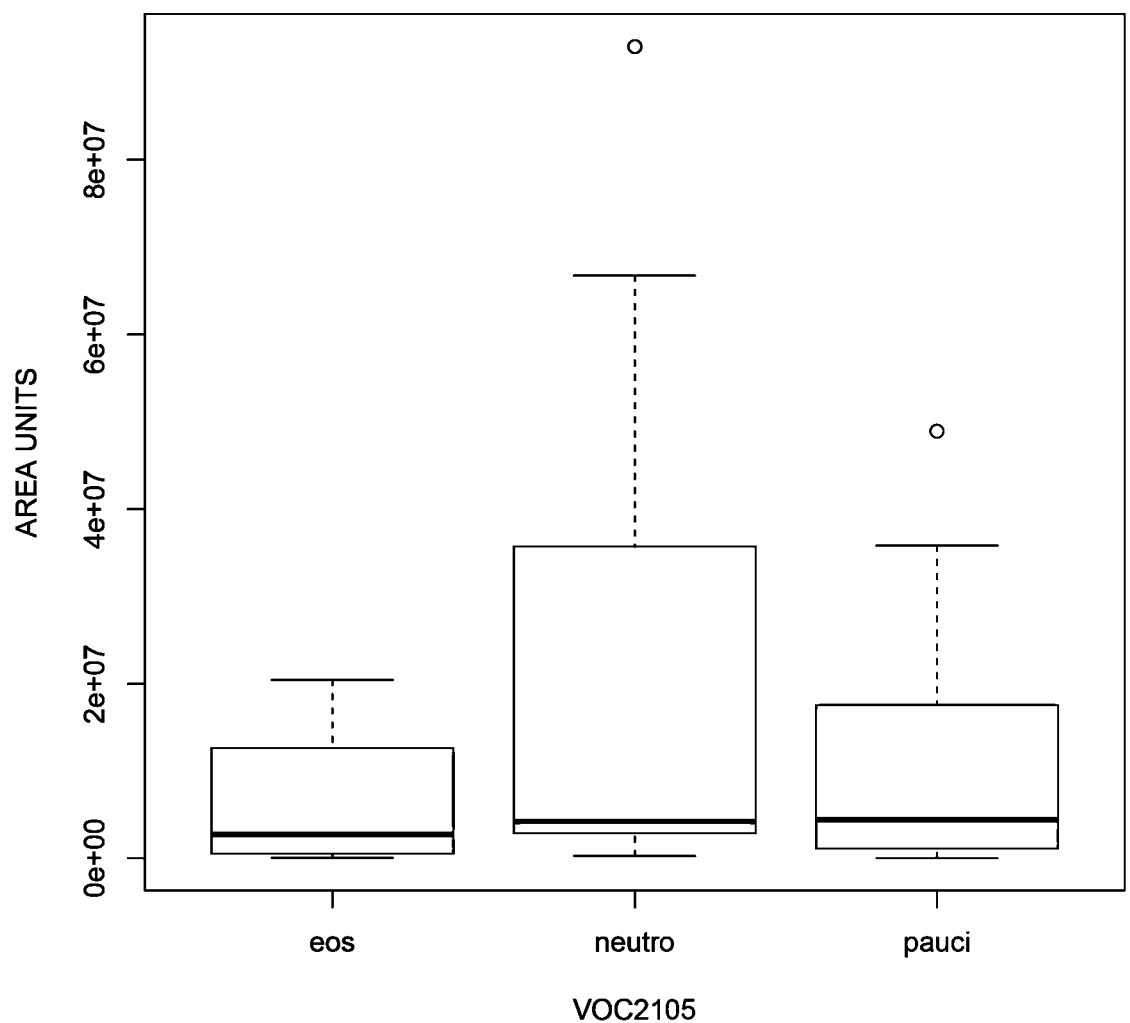
FIG. 11: represent the boxplot of VOC 2105 relative abundances across different asthma inflammatory subtypes with black line representing median.

The area under the peak is related to the concentration of the compounds in the exhaled air. The mean area for neutrophilic subgroup Area(nonanal)$_{neutro}$ is 5816122 with P(area(nonanal)>0)$_{neutro}$=0.26. It means that 26% of the neutrophilic asthmatics have a nonanal peak in their exhaled breath. In eosinophilic subgroup, the Area(nonanal)$_{eos}$ is 731438 with P(area(nonanal)>0)$_{eos}$=0.114. In neutrophilic subgroup nonanal is more probable to occur and is 1.5 times more abundant (FIG. 11, table 3). We found the same trend for as 3,7-dimethylnonane (FIG. 9, table 3) and 1-propanol (FIG. 10, table 3).

Hexane was also found to be discriminative between eosinophilic and neutrophilic asthma with increased concentration of this VOG in the neutrophilic subtype (FIG. 8, VOG 337).

TABLE 3

Medians and interquartile range of selected VOCs across asthma subtypes. Range represents the minimum and maximum values across samples.

| VOC ID | Name | eosinophilic | | neutrophilic | | paucigranulocytic | |
| --- | --- | --- | --- | --- | --- | --- | --- |
| | | median | range | median | range | median | range |
| VOC1913 | 3,7-dimethylnonane | 14,343,579.8 | [281761.4 . . . 51300063.9] | 66,581,500.8 | [541164.0 . . . 369464662.2] | 7,582,791.8 | [510810.8 . . . 373089283.8] |
| VOC2105 | nonanal | 2,748,879.4 | [46590.5 . . . 20446122.5] | 4,221,547.1 | [258528.6 . . . 92971916.8] | 4,436,001.4 | [26687.9 . . . 48914956.6] |
| VOC2376 | — | 3,183,497.6 | [55260.5 . . . 41619994.5] | 7,428,691.7 | [380302.9 . . . 162761993.1] | 2,938,262.2 | [98974.7 . . . 58771536.1] |
| VOC337 | hexane | 3,566,091.0 | [1187400.9 . . . 9199031.2] | 61,820,221.3 | [5591794.9 . . . 145235761.5] | 17,700,387.4 | [1043242.2 . . . 151239910.0] |
| VOC253 | 1-propanol | 25,033,648.06 | [1454827.9 . . . 496084254.4] | 84,535,600.6 | [11907802.5 . . . 1605795627.0] | 29,897,659.98 | [15536082.4 . . . 690601845.3] |
| VOC903 | 2-hexanone | 283,156.8 | [38980.3 . . . 26647432.2] | 806,180.0 | [416078.9 . . . 1015067.2] | 4,388,495.2 | [14046.7 . . . 15242988.7] |
| VOC923 | unknown | 515,949.6 | [101603.0 . . . 3457686.3] | 644,869.0 | [19752.0 . . . 3898702.8] | 638,517.7 | [17995.5 . . . 23219742.4] |
| VOC2622 | 3-tetradecene | 2,167,594.0 | [87808.5 . . . 94253854.0] | 7,618,566.1 | [376523.1 . . . 58965486.5] | 869,755.9 | [133144.9 . . . 6293583.5] |
| VOC2853 | 1-pentadecene (C15H30) | 3,754,822.4 | [74399.9 . . . 44342211.8] | 8,955,716.6 | [103856.3 . . . 305653231.9] | 2,095,498.1 | [150744.7 . . . 35967432.8] |

Figure 12:
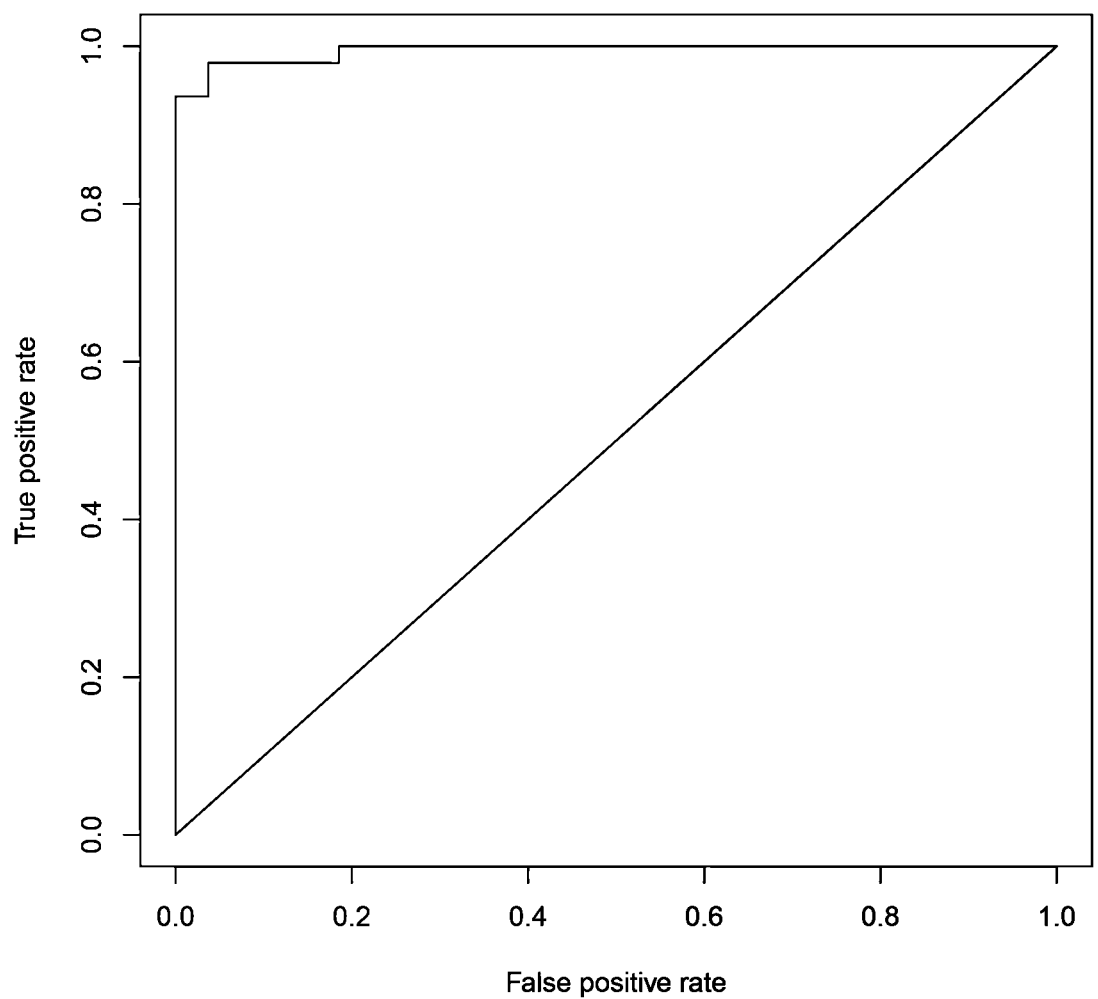
FIG. 12: represents ROC curve of eosinophilic and paucigranulocytic asthma discrimination using the whole forest of conditional inference trees representing the classification model. The area under ROC is 0.9945. The diagonal line represents random guessing.

We constructed AUROC and AUPR (precision versus recall) for the eosinophilic versus paucigranulocytic asthma, neutrophilic versus paucigranulocytic asthma and for eosinophilic versus neutrophilic classification tasks. First, the whole forest of trees representing the classification model was used to construct 3 ROG curves (example of classification model discriminating between eosinophilic and paucigranulocytic asthma in FIG. 12). Our results were very close to the theoretical classification performance maximums (table 4).

TABLE 4

ROC and PR curves for classification models between inflammatory subtypes.

| Classification model | AUC |
| --- | --- |
| Eosinophilic versus paucigranulocytic | |
| ROC | 0.9945 |
| PR | 0.9757 |
| Neutrophilic versus paucigranulocytic | |
| ROC | 0.8459 |
| PR | 0.4399 |

TABLE 4-continued

ROC and PR curves for classification models between inflammatory subtypes.

| Classification model | AUC |
| --- | --- |
| Eosinophilic versus neutrophilic asthma | |
| ROC | 0.9193 |
| PR | 0.2582 |

We also looked at the top ranked compounds that gave alone very good classification accuracy. In the eosinophilic versus neutrophilic classification, 3,7-dimethylnonane (VOC1913) gave the highest average accuracy of 73.0%, precision of 71.9%, sensitivity of 100% and specificity of 12.2% (Table 5). In eosinophilic versus paucigranulocytic classification, 2-hexanone (VOC903) achieved the highest performance amongst other considered VOCs with accuracy and precision reaching 62.3% and 61.6% values (Table 5). In the paucigranulocytic against neutrophilic classification, the 3-tetradecene (VOC2622) achieved the highest performance amongst other VOCs with accuracy and precision reaching 72% and 70% values (Table 5). The provided estimates were obtained based on 10 cross-validation runs each containing 35% of available samples.

TABLE 5

The binary classification performances based on individual VOCs. FDR: false discovery rate.

| VOC ID | Name | classification | sensitivity | specificity | FDR | precision | accuracy |
| --- | --- | --- | --- | --- | --- | --- | --- |
| VOC1913 | 3,7-dimethylnonane | eos vs neutro | 1.000 | 0.122 | 0.281 | 0.719 | 0.730 |
| VOC2105 | nonanal | eos vs neutro | 0.955 | 0.120 | 0.272 | 0.728 | 0.715 |
| VOC253 | 1-propanol | eos vs neutro | 0.966 | 0.086 | 0.277 | 0.723 | 0.712 |
| VOC337 | hexane | eos vs pauci | 1.000 | 0.059 | 0.420 | 0.580 | 0.591 |
| VOC903 | 2-hexanone | eos vs pauci | 0.981 | 0.087 | 0.384 | 0.616 | 0.623 |
| VOC923 | unknown | eos vs pauci | 0.972 | 0.096 | 0.397 | 0.603 | 0.609 |
| VOC2622 | 3-tetradecene | pauci vs neutro | 1.000 | 0.196 | 0.300 | 0.700 | 0.720 |
| VOC2853 | 1-pentadecene | pauci vs neutro | 0.929 | 0.256 | 0.318 | 0.682 | 0.682 |

The invention claimed is:

1. A method of treatment of neutrophilic airway inflammation in a subject, wherein the airway inflammation is asthma, comprising the steps of:
   a) determining whether the subject is in need of receiving neutrophilic asthma treatment by performing an in vitro procedure of diagnosing, prognosing and/or monitoring neutrophilic asthma in the subject, comprising the sub-steps of:
      a1) determining an amount of one or more volatile organic compounds (VOCs) in a sample of exhaled breath from the subject;
      a2) comparing the amount of the one or more VOCs with a reference value, the reference value representing a known diagnosis, prognosis and/or monitoring status of neutrophilic asthma;
      a3) finding a deviation or no deviation of the amount of said one or more VOCs from the reference value; and
      a4) attributing said finding of deviation or no deviation to a particular diagnosis, prognosis and/or monitoring status of neutrophilic asthma in the subject;
   b) treating the subject diagnosed, prognosed and/or monitored in step a) as being in need of neutrophilic asthma treatment with a treatment selected from the group consisting of macrolides, anti-leukotriene agents, bronchodilators, and combinations thereof;
   wherein the one or more volatile organic compounds (VOCs) is/are selected from the group consisting of:
      3-tetradecene, and
      1-pentadecene; and the method discriminates neutrophilic asthma from paucigranulocytic asthma in the subject; and
   wherein:
      the reference value is the amount of the same one or more VOCs in a sample of exhaled breath from the subject suffering from paucigranulocytic asthma; and wherein
      an elevated amount of said one or more VOCs from said reference value is diagnostic or prognostic of neutrophilic asthma and/or of absence of paucigranulocytic asthma in the subject.

2. A method of treatment of neutrophilic airway inflammation in a subject, wherein the airway inflammation is asthma, comprising the steps of:
   a) determining whether the subject is in need of receiving neutrophilic asthma treatment by performing an in vitro procedure of diagnosing, prognosing and/or monitoring neutrophilic asthma in the subject, comprising the sub-steps of:
      a1) determining an amount of one or more volatile organic compounds (VOCs) in a sample of exhaled breath from the subject;
      a2) comparing the amount of the one or more VOCs with a reference value, the reference value representing a known diagnosis, prognosis and/or monitoring status of neutrophilic asthma;
      a3) finding a deviation or no deviation of the amount of said one or more VOCs from the reference value; and
      a4) attributing said finding of deviation or no deviation to a particular diagnosis, prognosis and/or monitoring status of neutrophilic asthma in the subject;
   b) treating the subject diagnosed, prognosed and/or monitored in step a) as being in need of neutrophilic asthma treatment with a treatment selected from the group consisting of macrolides, anti-leukotriene agents, bronchodilators, and combinations thereof;
   wherein the one or more volatile organic compounds (VOCs) is/are selected from the group consisting of:
      3-tetradecene, and
      1-pentadecene; and the method discriminates neutrophilic asthma from paucigranulocytic asthma in the subject; and
   wherein:
      the reference value is the amount of the same one or more VOCs in a sample of exhaled breath from the subject suffering from neutrophilic asthma; and wherein
      no deviation of the amount of said one or more VOCs from said reference value is diagnostic or prognostic of neutrophilic asthma and/or of absence of paucigranulocytic asthma in the subject.

* * * * *